United States Patent
Sauer

(10) Patent No.: US 7,833,237 B2
(45) Date of Patent: Nov. 16, 2010

(54) INSTRUMENT FOR ASSISTING IN THE REMOTE PLACEMENT OF TIED SURGICAL KNOTS AND TRIMMING OF SUTURE AWAY FROM THE KNOT AND METHOD OF USE

(75) Inventor: Jude S Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 1499 days.

(21) Appl. No.: 10/543,948

(22) PCT Filed: Feb. 4, 2004

(86) PCT No.: PCT/US2004/003069

§ 371 (c)(1),
(2), (4) Date: Aug. 1, 2005

(87) PCT Pub. No.: WO2004/069291

PCT Pub. Date: Aug. 19, 2004

(65) Prior Publication Data

US 2006/0161183 A1    Jul. 20, 2006

Related U.S. Application Data

(60) Provisional application No. 60/444,935, filed on Feb. 4, 2003.

(51) Int. Cl.
*A61B 17/04* (2006.01)
(52) U.S. Cl. .................. 606/148; 606/139; 606/144
(58) Field of Classification Search .................. 606/139, 606/144–148
See application file for complete search history.

(56) References Cited

U.S. PATENT DOCUMENTS

| | | | | |
|---|---|---|---|---|
| 2,363,334 A | * | 11/1944 | Jones | 606/147 |
| 3,985,138 A | * | 10/1976 | Jarvik | 606/231 |
| 5,015,250 A | * | 5/1991 | Foster | 606/147 |
| 5,084,058 A | * | 1/1992 | Li | 606/148 |

(Continued)

OTHER PUBLICATIONS

Suture Assistant—Endoscopic Suturing Device, Johnson and Johnson Gateway, printout from website at http//www/jnjgateway/com/home.jhtml?loc=USENG, Mar. 30, 2006.

(Continued)

*Primary Examiner*—Darwin P Erezo
(74) *Attorney, Agent, or Firm*—Kenneth J. Lukacher

(57) ABSTRACT

An instrument is provided having a shaft extending to a distal end having a cavity, and a passageway extending to the cavity through which a first suture end of a suture loop extends from a tissue site to facilitate a user looping a second suture end around the first suture end between the tip and the site to form a knot. Advancing of the distal tip while drawing the first suture end through the passageway pushes the knot to the site. The distal tip of another embodiment adds another passageway through which the second suture end is passed to assist in forming and pushing a knot at to the tissue site. The distal end has two openings through which two suture ends are passed from the placed knot, and a blade in the distal end is positionable to cut the suture ends near the knot.

7 Claims, 25 Drawing Sheets

U.S. PATENT DOCUMENTS

| | | | | |
|---|---|---|---|---|
| 5,087,263 A | * | 2/1992 | Li | 606/148 |
| 5,133,723 A | * | 7/1992 | Li et al. | 606/148 |
| 5,163,946 A | * | 11/1992 | Li | 606/148 |
| 5,176,691 A | * | 1/1993 | Pierce | 606/148 |
| 5,211,650 A | * | 5/1993 | Noda | 606/139 |
| 5,217,471 A | * | 6/1993 | Burkhart | 606/148 |
| 5,292,327 A | * | 3/1994 | Dodd et al. | 606/148 |
| 5,324,298 A | * | 6/1994 | Phillips et al. | 606/148 |
| 5,330,488 A | * | 7/1994 | Goldrath | 606/148 |
| 5,334,200 A | * | 8/1994 | Johnson | 606/148 |
| 5,342,369 A | * | 8/1994 | Harryman, II | 606/96 |
| 5,386,601 A | | 11/1994 | Sauer et al. | |
| 5,397,326 A | * | 3/1995 | Mangum | 606/148 |
| 5,405,352 A | * | 4/1995 | Weston | 606/148 |
| 5,423,837 A | * | 6/1995 | Mericle et al. | 606/148 |
| 5,431,666 A | | 7/1995 | Sauer et al. | |
| 5,507,757 A | | 4/1996 | Sauer et al. | |
| 5,520,702 A | * | 5/1996 | Sauer et al. | 606/144 |
| 5,562,684 A | * | 10/1996 | Kammerer | 606/139 |
| 5,562,686 A | * | 10/1996 | Sauer et al. | 606/144 |
| 5,643,289 A | * | 7/1997 | Sauer et al. | 606/139 |
| 5,669,917 A | * | 9/1997 | Sauer et al. | 606/139 |
| 5,766,183 A | * | 6/1998 | Sauer | 606/139 |
| 5,792,151 A | * | 8/1998 | Heck et al. | 606/144 |
| 5,846,254 A | | 12/1998 | Schulze et al. | |
| 6,077,278 A | * | 6/2000 | Mayer | 606/147 |
| 6,099,553 A | * | 8/2000 | Hart et al. | 606/232 |
| 6,152,934 A | | 11/2000 | Harper et al. | |
| 6,368,334 B1 | * | 4/2002 | Sauer | 606/139 |
| 6,488,690 B1 | * | 12/2002 | Morris et al. | 606/144 |
| 6,533,796 B1 | * | 3/2003 | Sauer et al. | 606/144 |
| 6,641,592 B1 | * | 11/2003 | Sauer et al. | 606/144 |
| 6,733,509 B2 | * | 5/2004 | Nobles et al. | 606/138 |
| 6,746,457 B2 | * | 6/2004 | Dana et al. | 606/148 |
| 6,921,408 B2 | * | 7/2005 | Sauer | 606/144 |
| 6,997,931 B2 | * | 2/2006 | Sauer et al. | 606/139 |
| 7,235,086 B2 | * | 6/2007 | Sauer et al. | 606/139 |
| 7,390,328 B2 | * | 6/2008 | Modesitt | 606/144 |
| 7,481,817 B2 | * | 1/2009 | Sauer | 606/170 |
| 2003/0204205 A1 | | 10/2003 | Sauer et al. | |
| 2004/0162572 A1 | | 8/2004 | Sauer | |
| 2005/0154402 A1 | | 7/2005 | Sauer et al. | |
| 2005/0154403 A1 | | 7/2005 | Sauer et al. | |

OTHER PUBLICATIONS

Quick-Stitch Endoscopic Suturing System, Pare Surgical, Inc., printout from web site at http://paresurgical.com/system.htm, Mar. 30, 2006.

Sew-Right SR 5 Brochure, LSI Solutions, 2003.

Ti-Knot TK 5 Brochure, LSI Solutions, 2003.

* cited by examiner

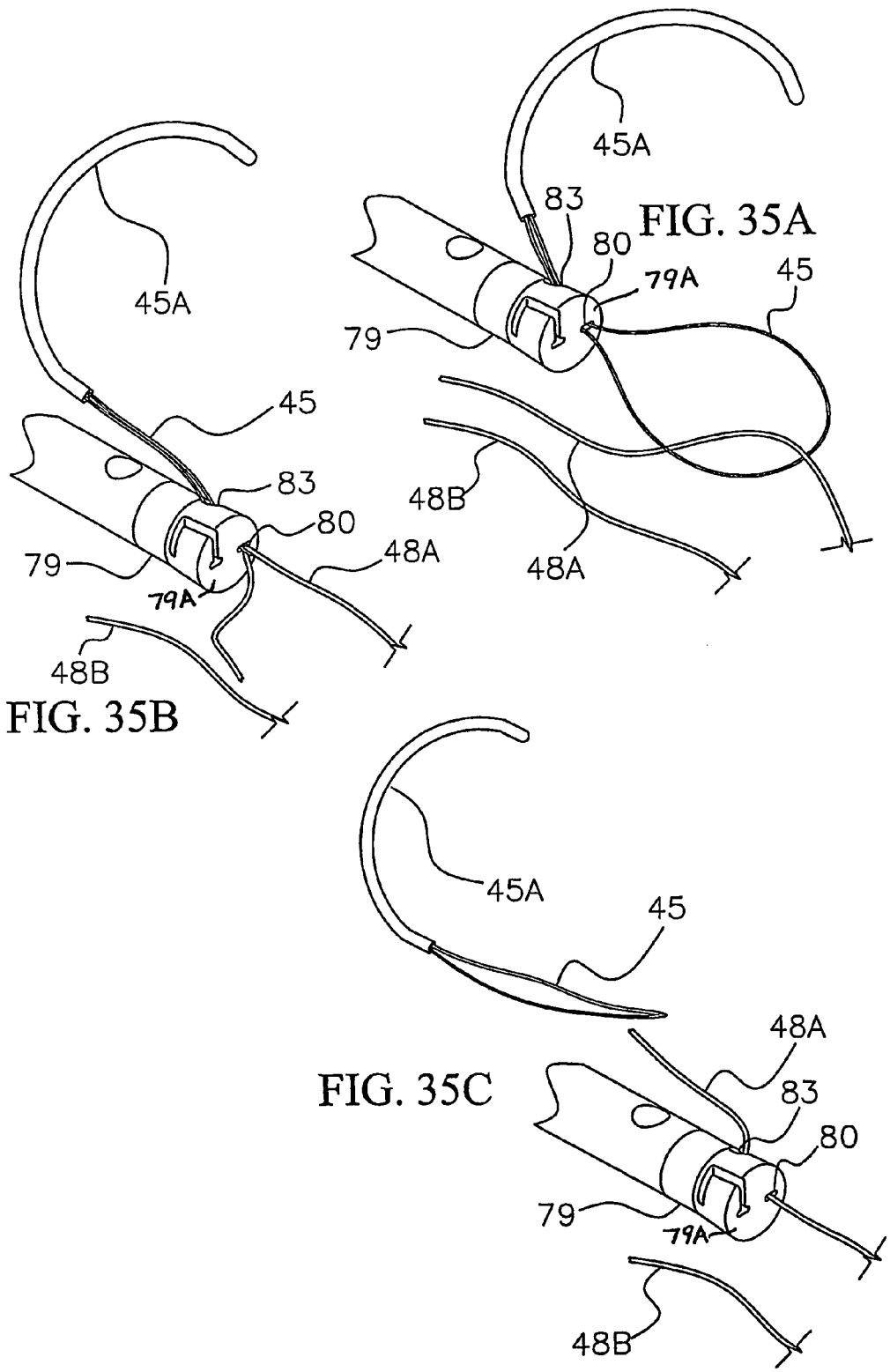

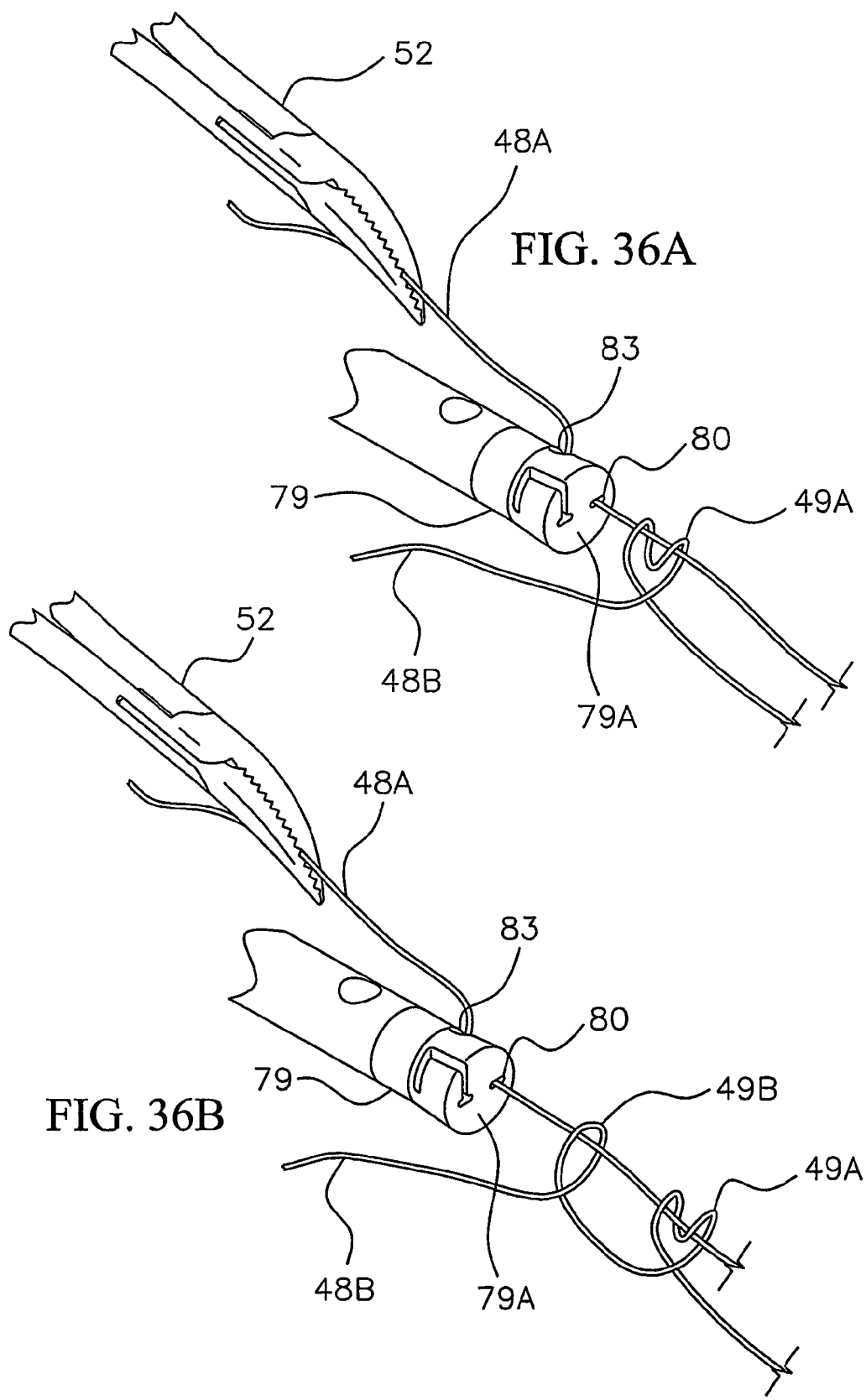

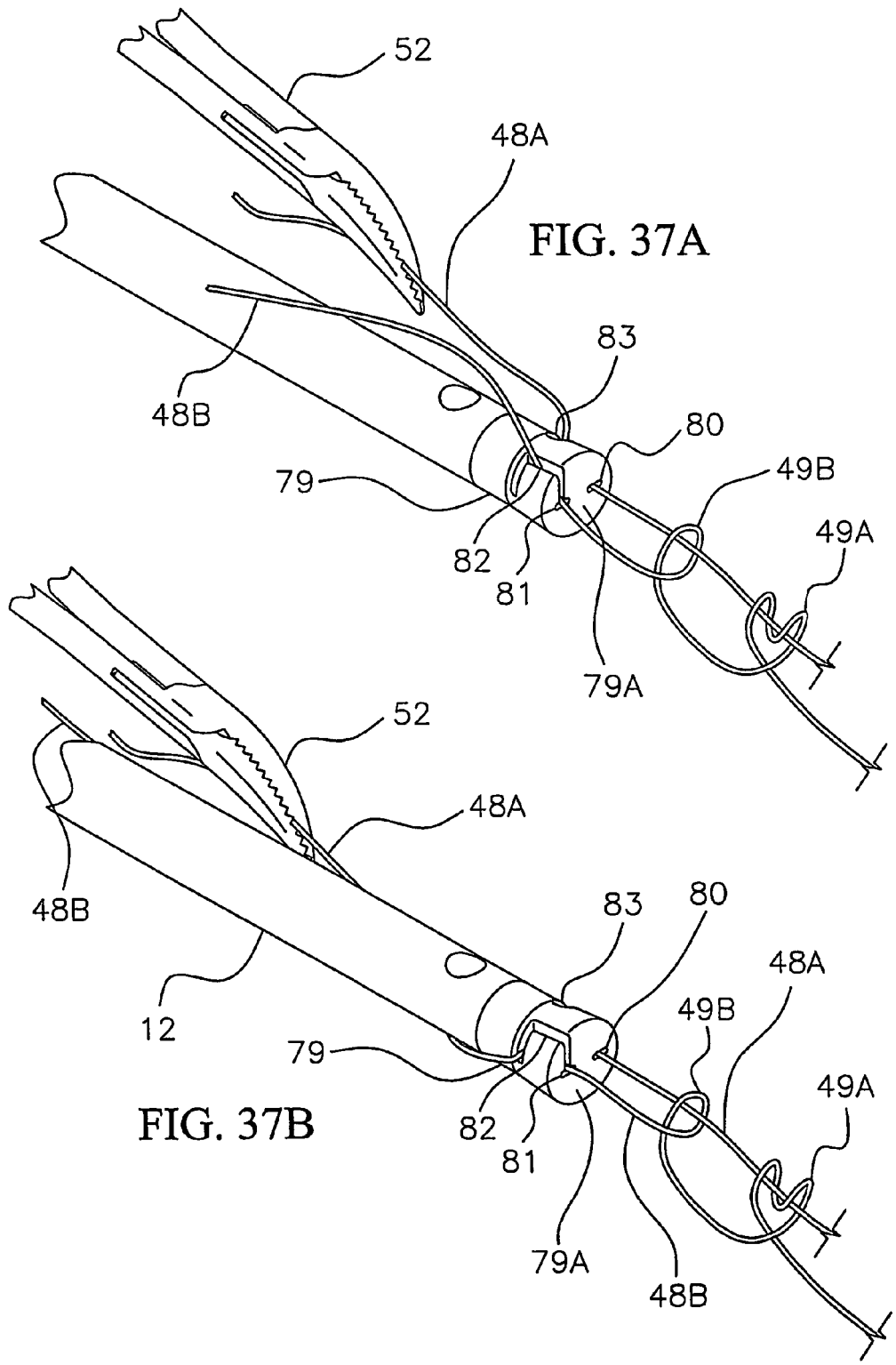

INSTRUMENT FOR ASSISTING IN THE REMOTE PLACEMENT OF TIED SURGICAL KNOTS AND TRIMMING OF SUTURE AWAY FROM THE KNOT AND METHOD OF USE

This application claims the benefit of priority to U.S. Provisional Patent Application No. 60/444,935, filed 4 Feb. 2003, which is herein incorporated by reference.

FIELD OF THE INVENTION

The present invention relates to an instrument, method, and system for surgically pushing hand-tied knots down to a wound closure site in tissue and then using the same instrument to trim excess suture away. The invention is useful for applying surgical knots to suture at remote locations in the body of a patient accessible through ports or cannulas. The instrument may also facilitate suture tying as is required for closing wounds through minimally invasive surgical techniques, such as laparoscopy, or through a single port, like a nephroscope, for a percutaneous pyeloplasty.

BACKGROUND OF THE INVENTION

A need exists for an improved surgical instrument to enable safer and more efficacious placement of hand tied knots at remote sites in the body. The use of suture or strings to aid in closing wounds has been known since ancient times. The suture tails left on top of a knot are cut away and removed from the patient in most surgical procedures, since they provide no structural function and are made of a material foreign to the body. With the advent of modern imaging technologies that permit surgical procedures to be conducted through small ports in the patient instead of through large open incisions, the hand tying of knots, sliding loops down the suture and trimming the suture tails at remote surgical sites can be quite challenging. Laparoscopically hand tied knots with conventional knot pushers have surprisingly high failure rates.

Conventional devices for pushing a throw of a knot down to tissue typically consists of a simple shaft with either a hole or a slot at its distal end. The benefits of a hole are that once the one end of the suture is placed through the hole, it cannot fall out while the suture is being passed down toward the wound site. However, under laparoscopic conditions, with gloved hands and bodily fluids on sutures, it is often difficult to pass the suture through a hole, so the holes in the distal end of many knot pushers are made large to facilitate easier suture passage during loading. However, holes that are large enough for unaided easy suture admittance often let the loop of knot slide through the hole while the instrument is being passed down towards the wound closure site. This trapping of the knot loop in the knot pusher hole can at times be problematic and often interrupts the flow of the knot tying procedure. An open slot at the distal end of a knot pusher makes it easier to load the suture (i.e., a hole does not need to threaded) prior to pushing the knot down, but very often the knot loop slips out of the slot and the loop is not adequately pushed down. The loop must be manually reloaded into the distal slot and attempt must again be made to slide the loop down to the wound closure site without it releasing from the slot.

The cutting of surgical suture at remote sites previously required an additional instrument, typically a long shafted scissors. The suture scissors often is introduced through a different port than the standard knot pusher. Use of another instrument for cutting suture thus requires another step, another port, and can be cumbersome and time consuming. To optimize surgical procedure efficacy, such cumbersome and time consuming repeated instrument exchanges should be minimized. Alternative devices are available that offer pre-tied knots either as a single closed loop (i.e. like a noose) or as pre-tied knot with one end of suture attached to a needle. The closed pre-tied (noose) loop does not enable passing the suture through a wound site, but just rather around available freely exposed tissue structures and does not offer a suture cutting option. The pre-tied suturing devices with attached needles, such as Quik-Stitch® (PARE Surgical, Inc., Englewood, Colo.) and Suture Assistant® (Ethicon Endo-Surgery, Inc., Cincinnati, Ohio), can be technically difficult to use, often have questionable knot security and also do not provide for a way of cutting the suture once the needle and its suture are pulled through the suture loop and the knot is tightened.

Instead of needles attached to pre-tied knots, which can be relatively awkward and unreliable, specialized suturing instruments, such as the SEW-RIGHT® SR. 5®. (made by LSI SOLUTIONS, Inc., Victor, N.Y.), may be used to accurately place suture prior to requiring knot tying. Technologies do exist to replace the need for hand tying in the form of the Ti-KNOT® device (by LSI SOLUTIONS, Inc., Victor, N.Y.). Instead of tying a knot by hand, this device crimps a piece of metal, typically titanium, around the sutures to secure them in place. Leaving behind metallic foreign materials is sometimes contraindicated under certain conditions. In the case of inside of the kidney's collecting system, a foreign material, such as titanium, may induce the formation of kidney stones. While such alternative surgical knot pushers exist to aid in remote suturing, they do not combine the features for knot pushing along with an integrated suture cutting mechanism.

SUMMARY OF THE INVENTION

The principal feature of the present invention is to provide an instrument, method, and system for facilitating the forming and pushing of surgical tied knots down towards a wound at a remote tissue site, in which the same instrument is used for cutting away redundant suture tails.

It is another feature of the present invention is to provide an instrument, method, and system for facilitating the forming and pushing of surgical tied knots down towards a wound at a remote tissue site which for laproscopic or percutaneous pyeloplasty surgical procedures, where the instrument may be passed through a cannula in the patient or a port of another instrument.

It is still another feature of the present invention to provide an improved method for loading suture through a knot pusher instrument using a loop snare tool.

It is a further feature of the present invention to provide an improved method for forming a knot to close a tissue would site using a double loop and a single loop of suture.

Briefly described, the present invention embodies an instrument having a proximal end with a housing, a shaft extending from the housing to a distal end to enable remote placement of the distal end in the body of a patient having tissue, such as a wound site, from which a loop of suture with two ends extends, and a distal tip at the distal end having a distal surface capable of facing the tissue. The distal tip has a hole or opening extending from the distal surface to a cavity in the side of the distal tip. A first end of the suture is received through this hole, such as with the assistance of a tool with a snare loop, to enable a user to loop the second end of the suture about the first end of said suture to form one or more knots. The distal tip when advanced pushes these knots as they slide along the first end of the suture to the tissue, while the first end of the suture is being drawn through the hole. Two openings are provided at the distal end through which the first and second ends of the suture are received through, such as also with assistance of the snare loop tool, after placement of the knots to the tissue. The distal end has a blade movable from a retracted position to a forward position to cut (or trim) the suture extending through these two openings, in which movement of the blade between its retracted and forward positions is remotely controlled at the housing.

As a safety feature, the slide hole at the distal end of the instrument used to slide the suture knots to the tissue, and the openings used to trim, are not the same, so that the risk of inadvertently cutting the suture can be minimized.

A method and system using this instrument is also provided by the present invention.

The instrument of the present invention avails itself readily to laparoscopic procedures using a laparoscope and camera system for visualization and requiring extracorporeal knot tying through multiple ports. For example, in small bowel gastric bypass surgery where multiple knots can be tied adjacent to the jejunum on the small bowel closure, these knots could be tied and slid down using the invention and suture tails readily trimmed. An even more challenging application is illustrated below to show the use of the present invention for knot tying through a single port.

The closure of a percutaneous pyeloplasty wound at a stenotic ureteral pelvic junction using only a single nephroscope through which to pass instruments is a very challenging procedure, because traditional suture tying and trimming have been almost unfeasible under nephroscopic conditions. A nephroscope can have a working channel through which surgical instruments can be passed. Other technologies are existent that provide for the surgical cutting open of the wound (e.g., the CUT-GUIDE™ by LSI SOLUTIONS, Inc., Victor, N.Y.) and for the accurate placement of suture through the wound prior to tying (e.g., the SEW-RIGHT®SR. 5® by LSI SOLUTIONS, Inc., Victor, N.Y.). Once the suture is placed in a site like this through a nephroscope, surgeons often struggle to accurately tension the suture, appose the wound edges, create the loops that will constitute the knot and then slide those loops down. Under these conditions, it is even difficult to get an instrument down to cut suture tails through the single port of a nephroscope.

Once the suture ends have been placed at the appropriate tissue wound closure site, the instrument of the present invention is passed to the surgeon. One suture end is placed through a wire snare extending through the distal slide hole in the end of the instrument. Using a curved handle on the wire snare, the wire snare and the one end of the suture are pulled through the suture hole at the end of the instrument. At this time, the wire snare and curved handle are passed off the field. Next, a surgical clamp (e.g., like a mosquito clamp) is put on the end of the suture that has passed through the hole. Depending on the preference for knot type as chosen by the surgeon, the opposite strand of suture is then wrapped around the suture that goes through the hole in a fashion known to make an acceptable surgical knot. Holding both ends of the suture outside of the body, the instrument is used to slide the loop of suture down to the wound closure site. The small suture hole at the instrument's distal end precludes the knot loop from also slipping into the suture hole, while sliding the loop towards the closure site; a smooth, contoured surface permitting smooth and unimpeded sliding of the knot down; a cut out or cavity in the distal tip that permits enhanced viewing of the knot within the viewable field of a laparoscope or a nephroscope under direct visualization. With the knot of suture now slid down to the wound closure site, both ends of the suture can be pulled upon to the appropriate tension by the surgeon, thereby accurately bringing the tissue edges together. The instrument is then slid back up the cannula with one clamped suture remaining through the suture hole. The next knot loop is then thrown by the surgeon and slid down to be placed on top of the first knot. This process may be repeated typically at least four times, to improve the overall knot security. The clamp is released from the one suture end. Both ends of the suture are then passed through the two openings at the distal end, thus orienting both strands of sutures substantially perpendicular to the length of the shaft at the distal end and in the path of the trimming blade. The instrument is then slid back down through the working channel of the nephroscope under direct visualization until the suture tails are at the desired length to the surgeon's preference. Under appropriate suture tension, the lever is squeezed, actuating the advancement of the suture trim blade down to the sutures and into a backstop behind the sutures. Both suture strands are completely transected. The lever is released pulling the blade back. The instrument is removed from the port along with the redundant suture tails. This knot loop tying, sliding and suture trimming process can be repeated for as many knots as necessary with the same instrument in the same patient. This invention can be a sterile single patient use instrument providing a pristine distal tip for sliding knots and ensuring a sharp and reliable blade for suture trimming.

In another embodiment of the present invention, the instrument has a different distal tip having two suture receiving passageways, slots or openings, rather than a single suture receiving hole or opening described above. Each of the passageways extends from the front distal surface through the distal tip to a different side of the distal tip, in which the first end of the suture is extended through a first of the passageways and then clamped to enable a user to wrap loop the second end of the suture about the first end in one loop or multiple (e.g., double) loop of the suture to form one or more knots. The second passageway is open along one side of the distal end to receive the second end of the suture, in which after the knots are formed the second end of the suture extending from the second passageway is at least partially wrapped around the distal end of the instrument's shaft and clamped when said distal tip is advanced to push the knots along the first end of the suture to the tissue, while the first end of the suture is being drawn through the first passageway. When removed from the first and second passageways, the ends of the suture may then be placed in the openings for cutting as described earlier. This method of using the instrument with the distal tip member of this embodiment is the same as described above, where the first passageway provides the features of the hole in the distal tip member, but when pushing one or more knots, the use of the two passageways from the distal surface for each of the suture ends minimizes the risk of premature lock of the knots before the tissue has been appropriately apposed with the knots.

The present invention also provides a method for forming a knot in two ends of suture extending from a tissue wound site by placing a first end of the suture through a hole or passageway along a distal end of an instrument (such as a conventional knot pusher instrument or the instrument of the present invention), wrapping the second end of the suture around the first end of the suture to form a double loop between the distal end of the instrument and the wound site, wrapping the second end of the suture around the first end of the suture to form a single loop between the distal end of the instrument and the double loop, pulling the first end of the suture away from the wound site while advancing the instrument to push the without tension of the second end of the suture to form a knot from the double loop and the single loop adjacent the wound site, and pulling of the second end of the suture to cause the double loop and the single loop of suture to lock the knot securely adjacent the wound site.

The present invention further provides a method for loading suture through a hole at the distal end of a conventional knot pusher instrument, or hole (or passageway) at distal end of the instrument of present invention, by inserting a loop of a snare tool through the hole of the knot pusher, locating one or both ends of the suture through the loop, retracting the loop through the hole, and releasing the end of suture from the loop to leave the suture through the hole.

BRIEF DESCRIPTION OF THE DRAWINGS

From the foregoing objects, features and advantages of the invention will become more apparent from a reading of the following description in connection with the accompanying drawings, in which:

FIG. 1A is an enlarged partial view of the distal end of the instrument of FIG. 1;

FIG. 2A is an enlarged partial view of the distal end of the instrument of FIG. 2 without suture;

FIGS. 3A and 3B are different perspective views of the distal end of the instrument of FIG. 3;

FIG. 15A is an exploded partial view of FIG. 15 broken away at the distal end of the instrument showing suture extending through two openings in the distal end prior to being cut;

FIG. 16A is an exploded partial view of FIG. 16 broken away at the distal end showing which suture extending through two openings at the distal end is cut by the blade of the instrument;

FIG. 35A is a right perspective view of the distal tip member of the instrument of FIG. 33A showing a wire snare placed through the non-open sided slot of the distal tip member;

FIG. 35B is a right perspective view of the distal tip member of the instrument of FIG. 33A showing a wire snare pulling one end of the suture back through the non-open sided slot;

FIG. 35C is a right perspective view of the distal tip member of the instrument of FIG. 33A showing one end of the suture now pulled through the non-open sided slot;

FIG. 36A is a right perspective view of the distal tip member of the instrument of FIG. 33A with a clamp on one end of the suture through the non-open sided slot and a double loop by the other end of the suture between the distal tip member and wound closure site;

FIG. 36B is a right perspective view of the distal tip member of the instrument of FIG. 33A with a clamp on one end of the suture through the non-open sided slot and showing an additional loop of suture placed between the distal tip member and a double loop;

FIG. 37A is a right perspective view of the distal tip member of the instrument of FIG. 33A showing one end of the suture from the loops being placed in the open-sided slot of the instrument;

FIG. 37B is a right perspective view of the distal tip member of the instrument of FIG. 33A showing the suture from the loops in the open-sided slot and passed under the distal tip member;

DETAILED DESCRIPTION OF THE INVENTION

Figure 1:
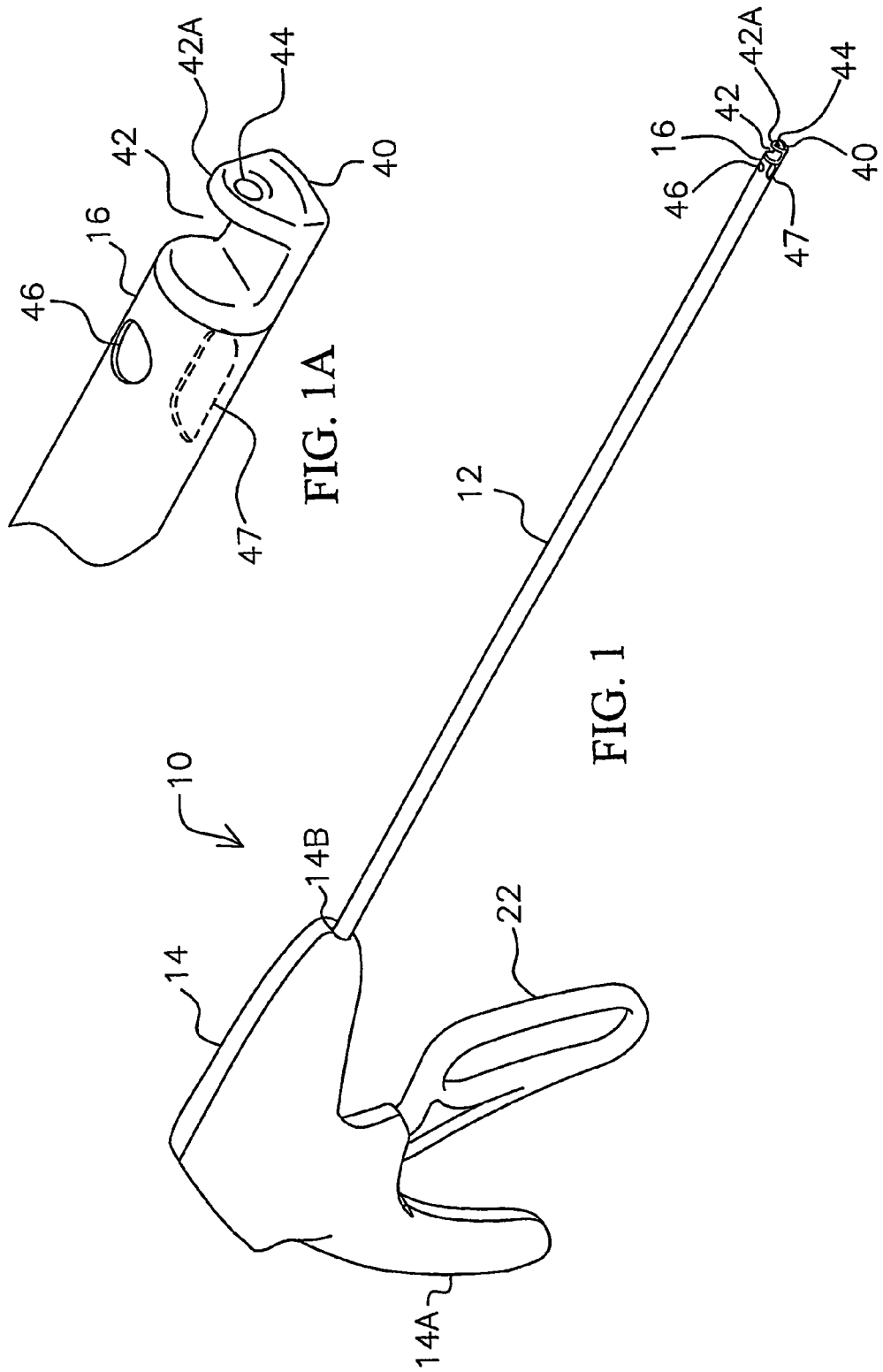
FIG. 1 is a perspective view of the instrument of the present invention with its lever in the forward position and the suture blade fully retracted back.

Referring to FIGS. 1, 1A, and 5-14, the instrument 10 of the present invention is shown having a shaft 12 extending from a housing 14 to a distal end 16. The housing is shaped like a pistol having a handle portion 14A, and may be made of a two-piece construction of molded plastic. Shaft 12 extends from opening 14B of the housing to distal end 16. The shaft 12 is provided by a rigid tube 18 (FIGS. 5 and 6) which at its D-shaped end 18A (FIG. 6) is registered into a corresponding shaped opening in an adapter 20, and a threaded nut 23 having an opening which extends over mounting tube 18 and screws onto the threaded end 21 of the adapter 20. The adapter 20 is mounted by flanges 20A in housing 12. A washer 31, such as of stainless steel, may be provided over tube 18 after nut 31 in housing 14. For example, tube 18 may be stainless steel and have an outer diameter of 5 mm. Shaft 12 may be rigid or flexible along all or part of its length to the distal end 16.

Figure 12:
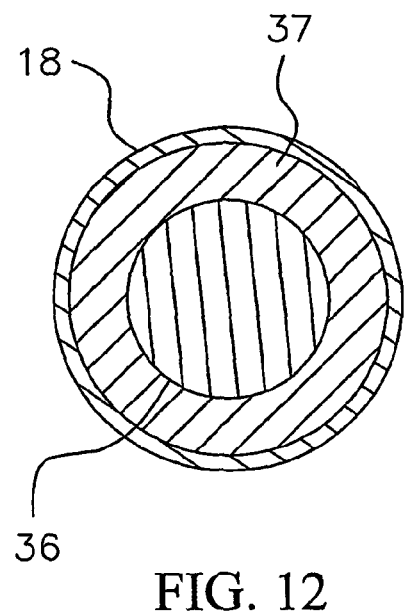
FIG. 12 is a cross-sectional view along lines 12-12 of the instrument of FIG. 5.
Figure 13:
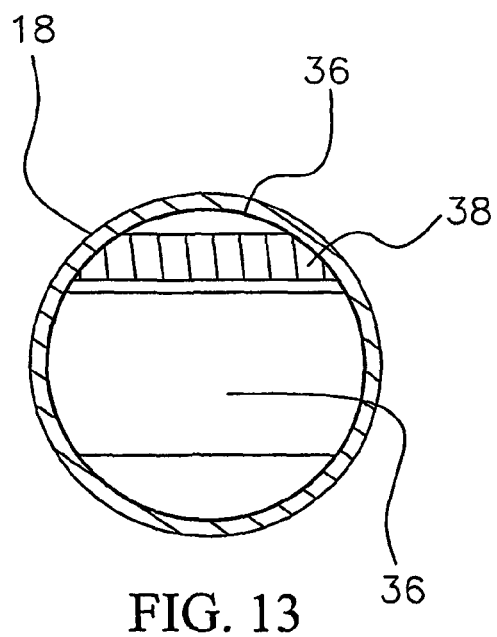
FIG. 13 is a cross-sectional view along lines 13-13 of the instrument of FIG. 5.

The instrument 10 includes an actuator member 22 representing a lever having two pins 22A extending into holes 15 in the sides of housing 14 upon which the actuator member 22 is pivotally mounted in the housing. Actuator member 22 has a portion which extends through an opening 14C in housing 14 to enable pivotal movement about pins 22a. An extension spring 24 is provided which hooks at one end in a notch 25 of actuator member 22 and is wound at the other end around a pin 26 located in holes 15A in the sides of housing 12, such that the actuator member 22 is spring biased to retain the actuator member normally in a forward position, as shown in FIG. 1. The body of housing 14 has a front portion 14D providing a stop that limits the pivotal movement of the actuator member 22. At the top of the actuator member 22 is a slot 27 provided by two flanges 28. A drive tube 30 is coupled to the actuator member 22 by a pin 32 received in holes 33 through flanges 28 and through holes 34 extending through end 30A of the drive tube 30. The drive tube 30 extends into tube 18 through adapter 20, via a bore 20B, and is attached to a blade driver 36 near the distal end 16 of the instrument 10. One end 36A of blade driver 36 has a diameter sized to be received into the open end 30B of drive tube 30, such that the edge 36B of the blade driver 36 abuts the edge of open end 30b, and is attached thereto by welding, brazing, or adhesive. Edge 36b, and the part of the blade driver adjacent thereto, has a diameter about the same as the outer diameter of drive tube 30, but less than the interior diameter of the tube 18. A gasket 37, or rubber ring, is located in an annular recess 36C of the blade driver 36 to provide a seal in tube 18 about the blade driver, but allowing the blade driver to be movable backward or forwards within tube 18. A cross-section through the gasket 37, blade driver 30, and tube 18 is shown in FIG. 12. The blade driver 36 extends to its other end 36B to form a blade 38 having a sharp cutting edge 39. The blade driver 36 and blade 38 may be of metal, such as stainless steel, and manufactured using electrical discharge machining (EDM) processes. A cross section through blade 38 is shown in FIG. 13.

Figure 2:
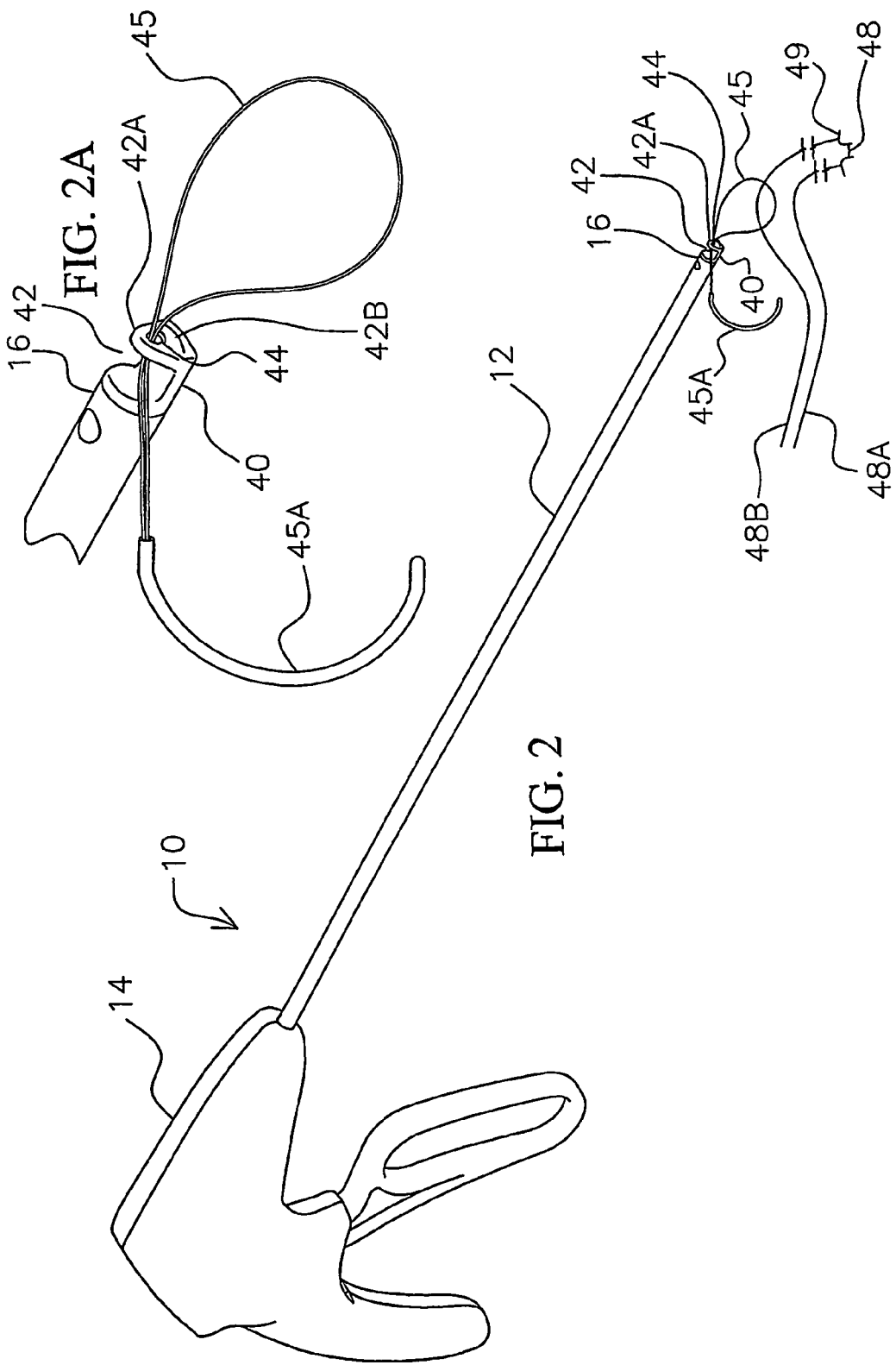
FIG. 2 is a perspective view of the distal end of the instrument of FIG. 1 showing the suture snare partially loaded through the suture hole.
Figure 14:
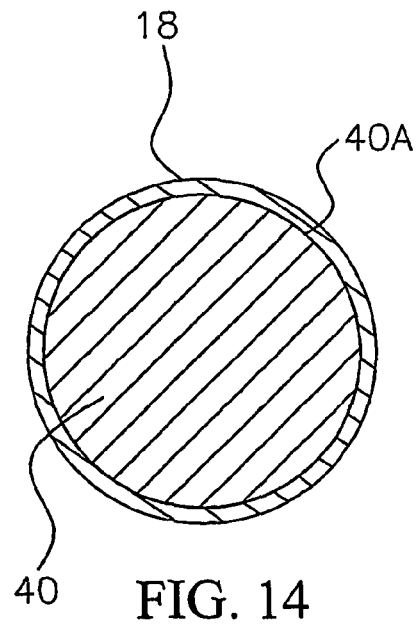
FIG. 14 is a cross-sectional view along lines 14-14 of the instrument of FIG. 5.

A distal tip member 40 is received into the open end 18B of the tube 18 at the distal end of the instrument, and has an end 40A of a diameter sized to be received in interior of tube 18 attached thereto by welding, brazing, or adhesive. A cross-section through the distal tip member 40 and tube 18 is shown in FIG. 14. The distal tip member 40 has a side open cavity 42 having a wall 42A and hole or opening 44 extending through this wall to provide an enclosed passageway to the cavity 42, such passageway being shown generally in a direction along the long axis of the shaft. Hole 44 is provided at the distal tip 40 of the instrument to assist a surgeon in locating one or more knots into the two free ends 48A and 48B of suture 48 which may extend through tissue 49, such as to close a wound in tissue of the body of a patient (FIGS. 2 and 2A). The front the wall 42A provides a distal surface 42B about hole 44 capable of facing such tissue when the distal end 16 with distal tip member 40 is located in the body of the patient. Hole 44 has a diameter which is sized to allow suture to pass there through, but smaller than the diameter of a knot made with such suture. The edges of wall 42A about hole 44 are smooth and tapered (beveled) to avoid snagging of suture, as shown in FIGS. 1A for example. A wire loop or snare 45 having a C-shaped handle 45A can pass through hole 44 of the distal tip member 40 (FIGS. 2 and 2A). One of the two ends 48A or 48B of suture 48 can be passed through the wire loop 45 (FIG. 2), such that when the wire loop is pulled one of the ends 48A or 48B is pulled through hole 44. Distal tip member 40 may be made, for example, of metal or plastic. The operation of the instrument 10 to locate knots will be described below in more detail in connection with FIGS. 17-28.

Figure 3:
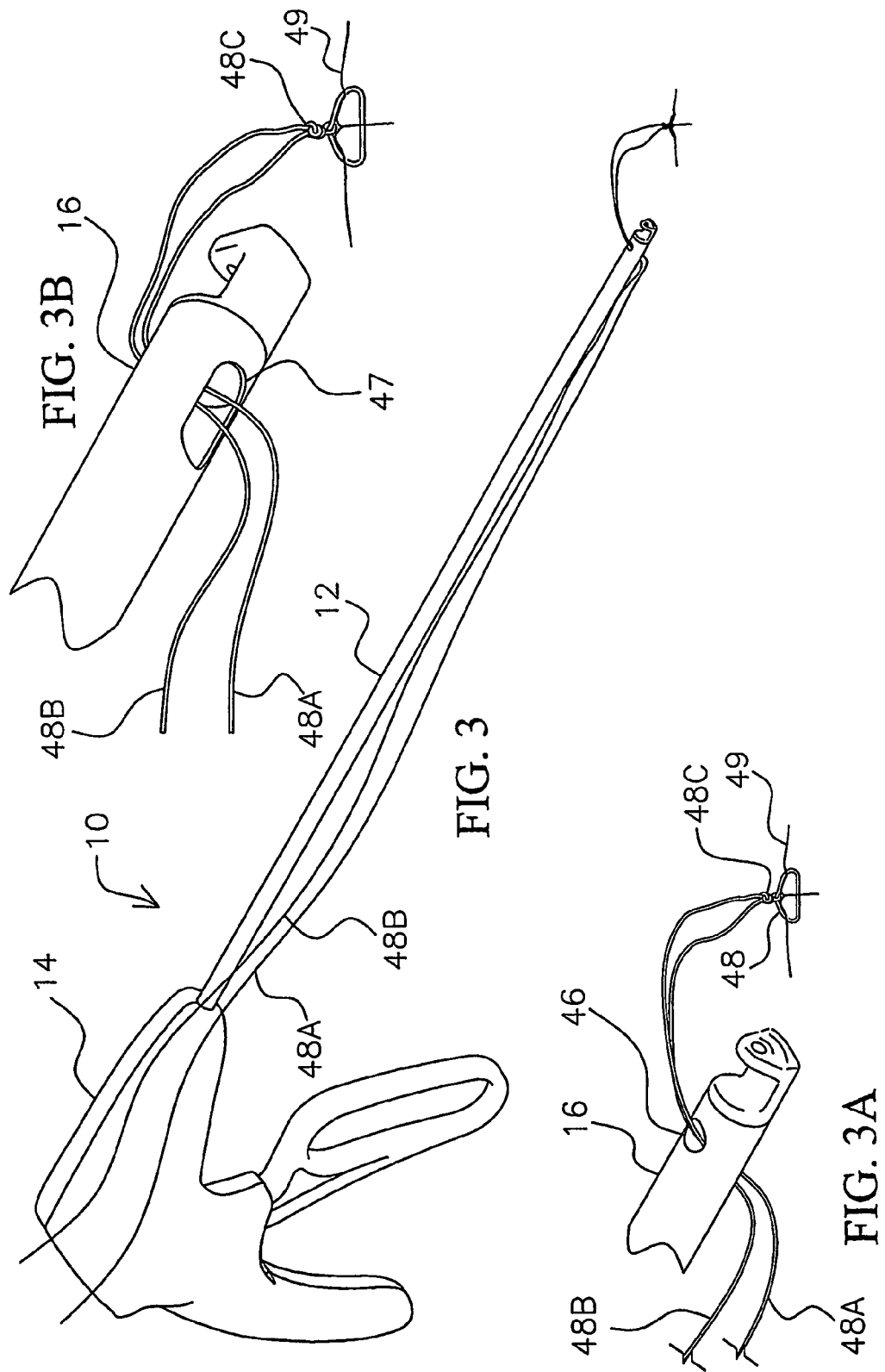
FIG. 3 is a perspective view of the instrument of FIG. 1 with the ends of the suture extended from knots through hole and slot of the distal end.
Figure 4:
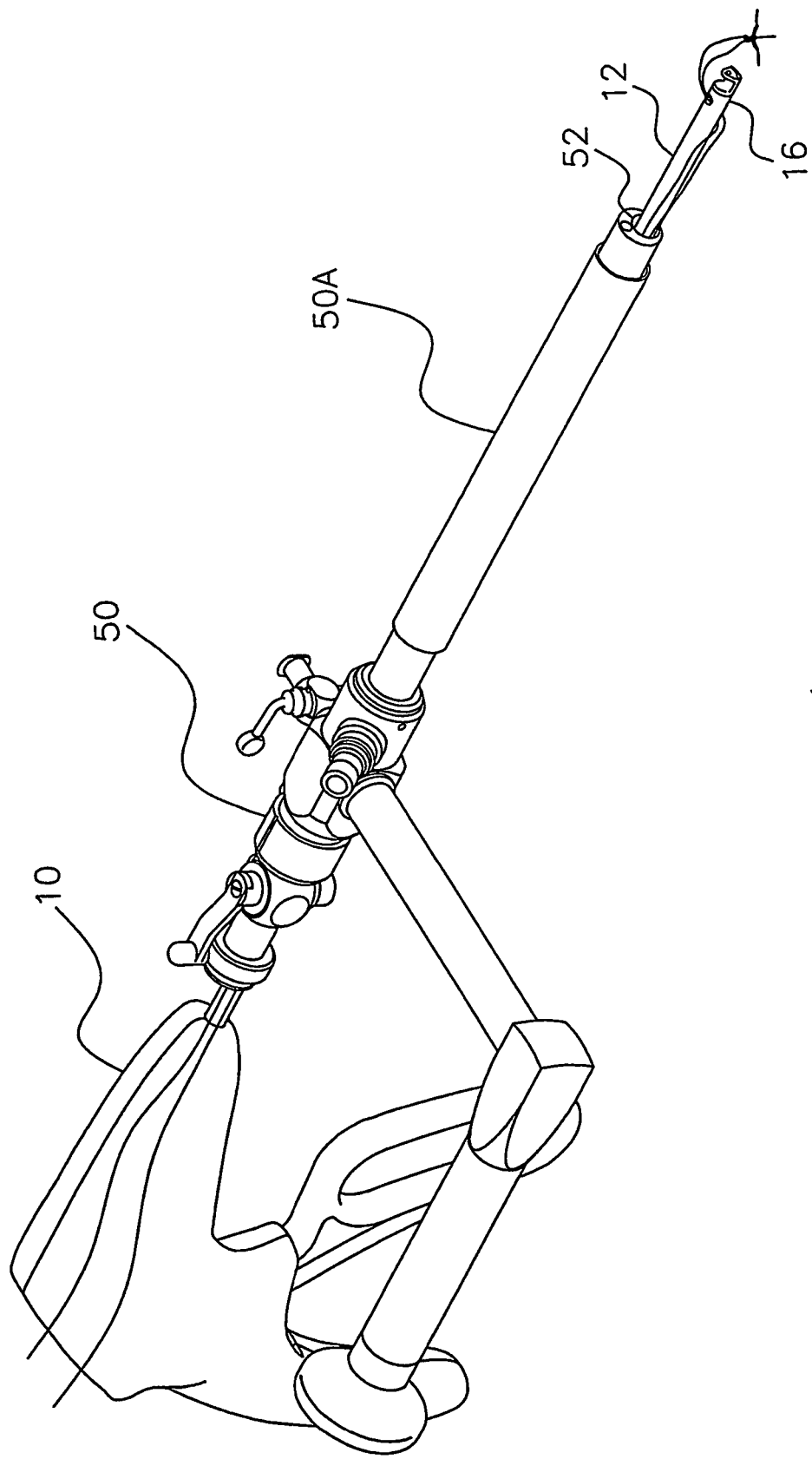
FIG. 4 is a perspective view of the instrument of FIG. 1 inserted through the working channel of a nephroscope.
Figure 5:
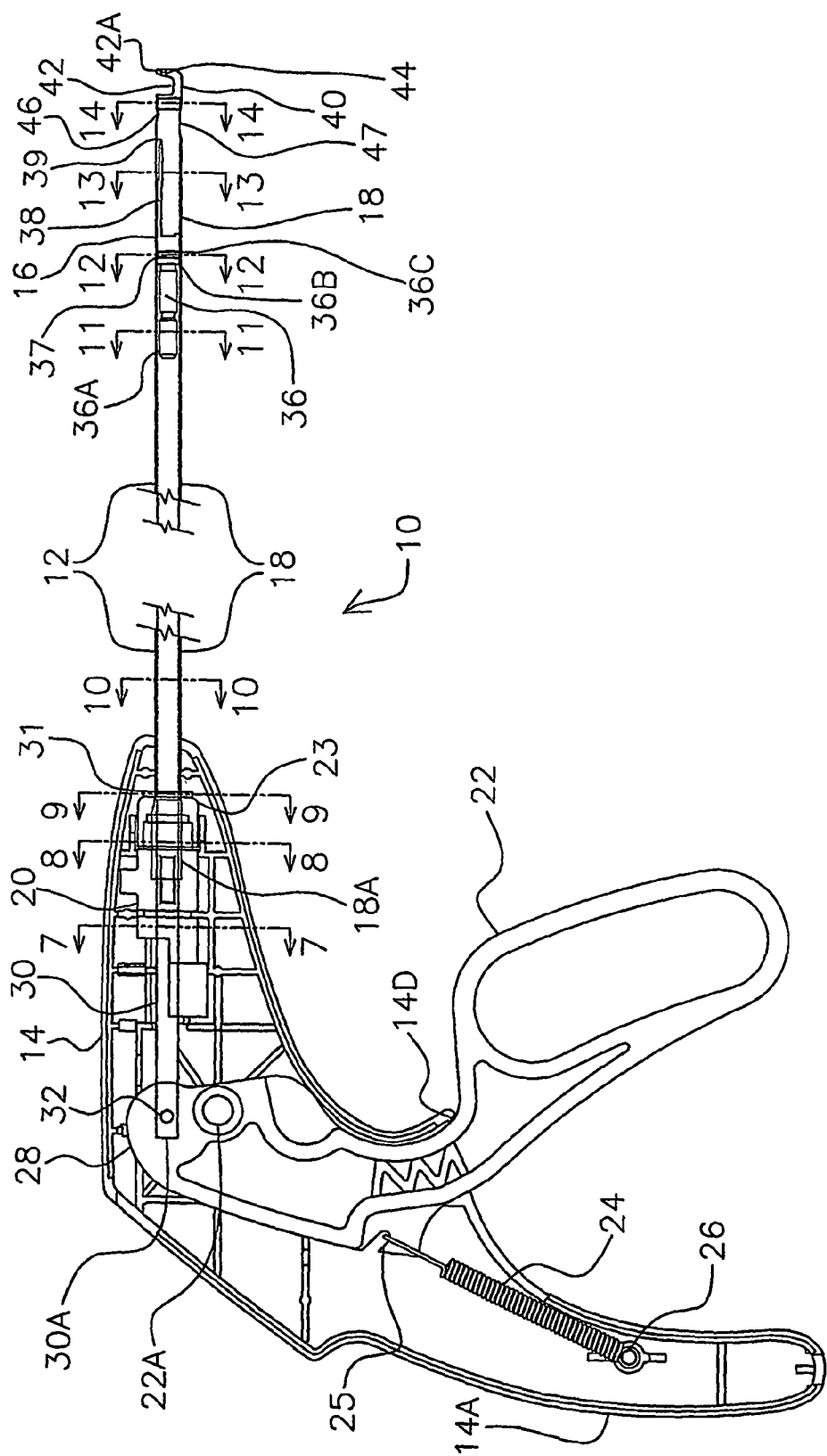
FIG. 5 is a side view of the instrument of FIG. 1 with the right half of the instrument's housing removed.
Figure 6:
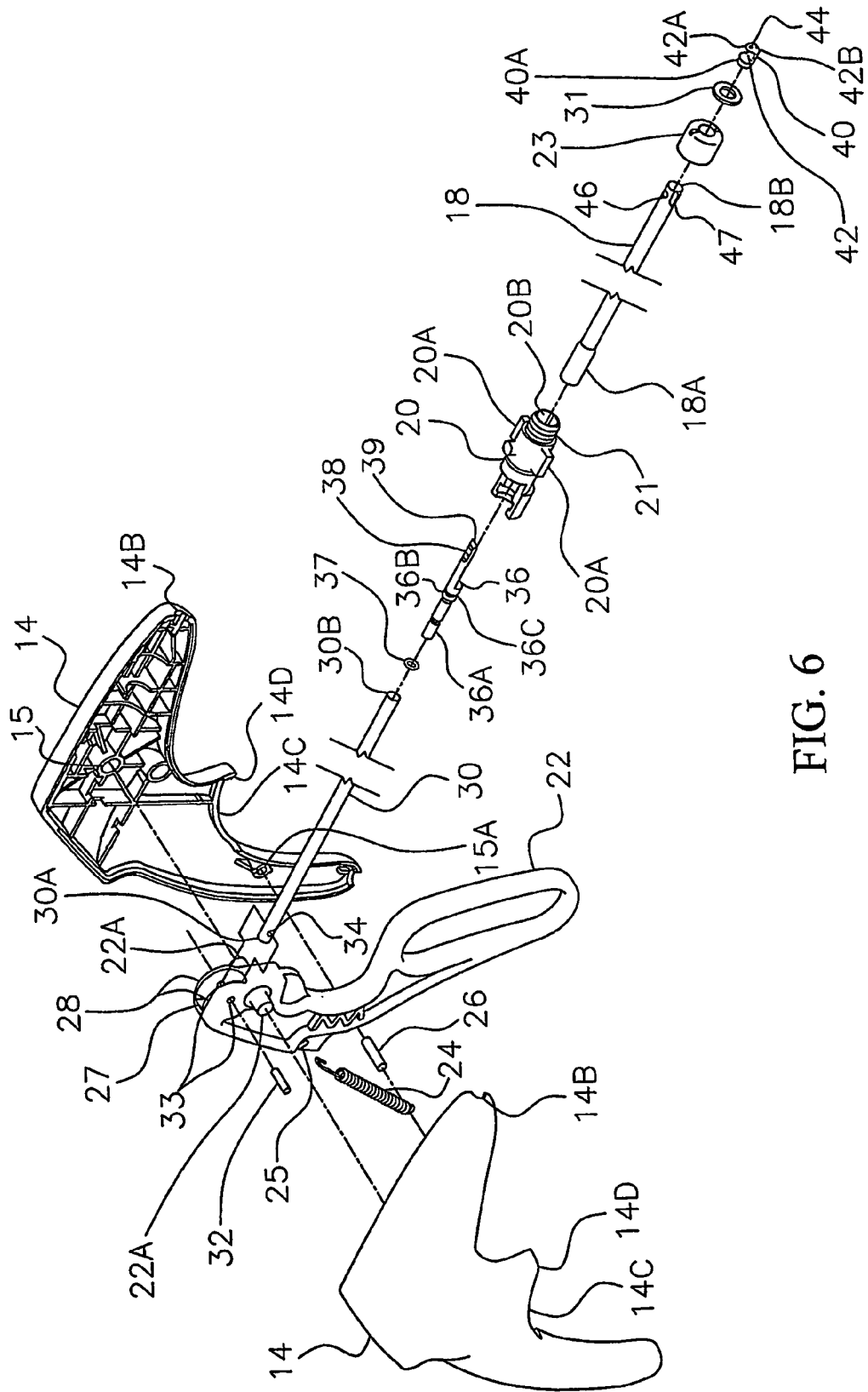
FIG. 6 is an exploded perspective view of the instrument of FIG. 1.
Figures 7, 8:
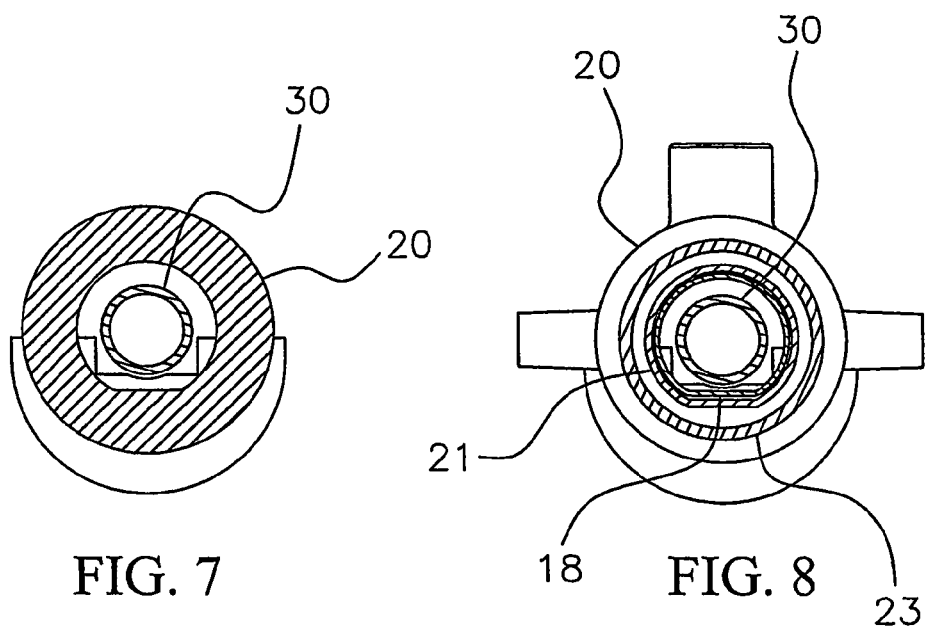
FIG. 7 is a cross-sectional view along lines 7-7 of the instrument of FIG. 5.
FIG. 8 is a cross-sectional view along lines 8-8 of the instrument of FIG. 5.
Figures 9, 10:
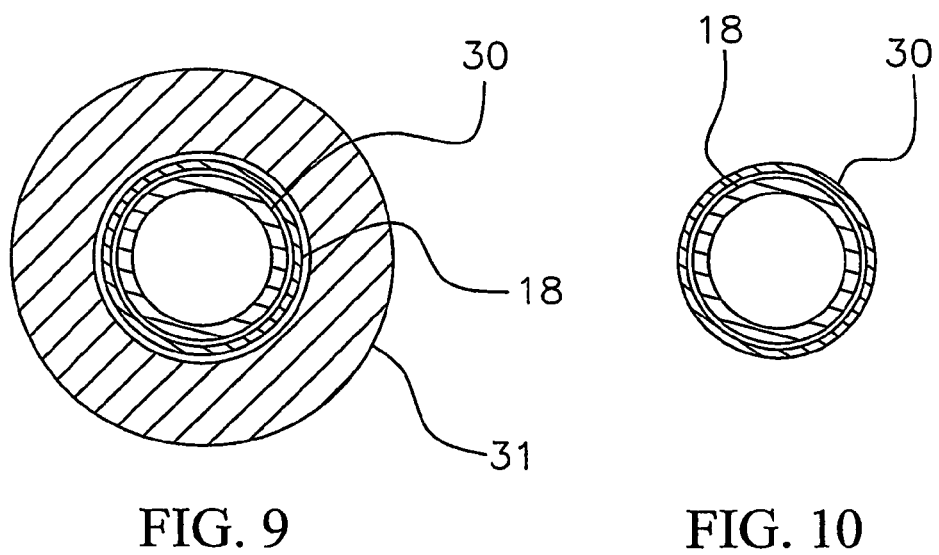
FIG. 9 is a cross-sectional view along lines 9-9 of the instrument of FIG. 5.
FIG. 10 is a cross-sectional view along lines 10-10 of the instrument of FIG. 5.
Figure 11:
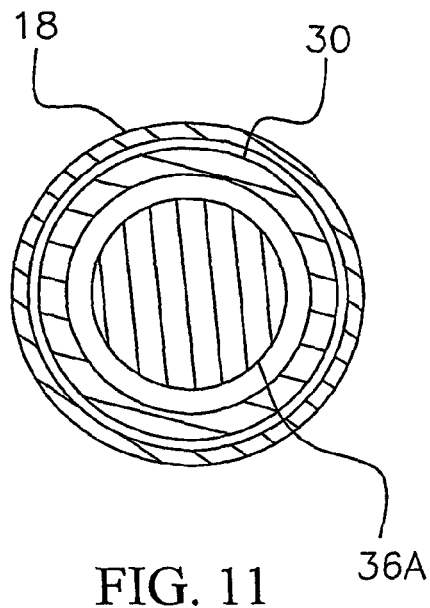
FIG. 11 is a cross-sectional view along lines 11-11 of the instrument of FIG. 5.
Figure 15:
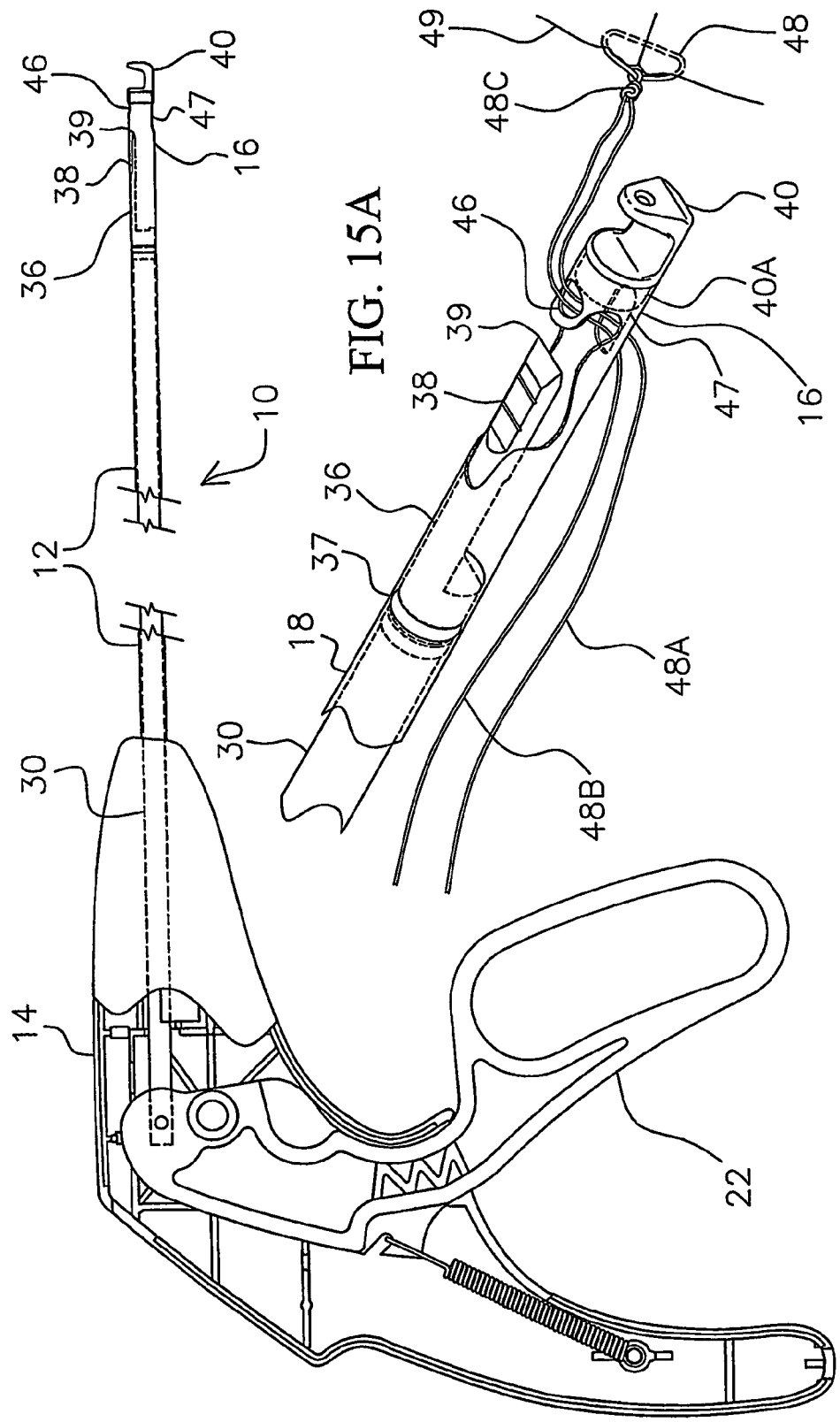
FIG. 15 is a side view of the instrument of FIG. 1 similar to FIG. 5 with the handle in the forward position and the blade retracted in the distal end of the instrument.
Figure 16:
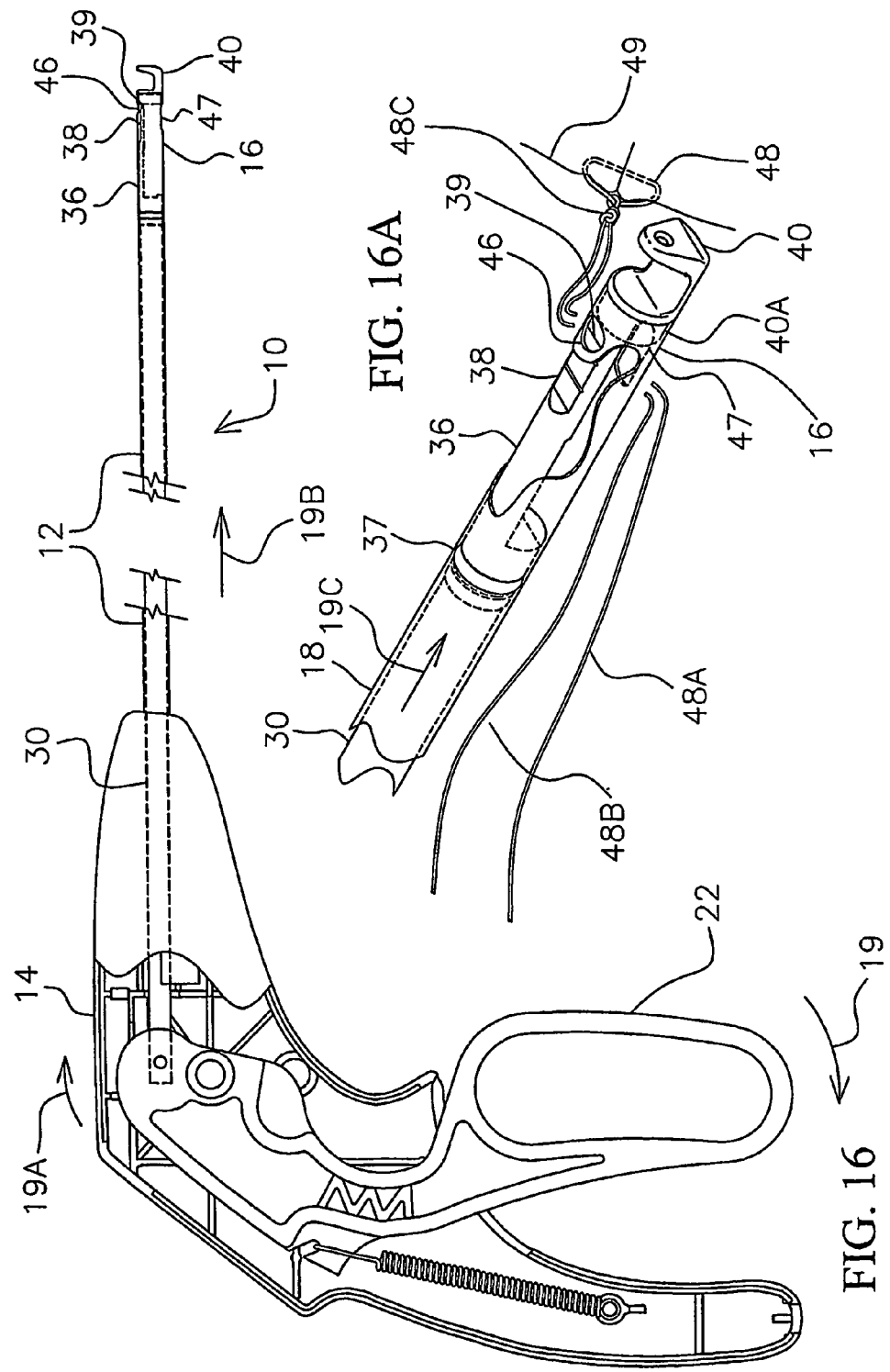
FIG. 16 is a side view of the instrument of FIG. 1 with the handle being pulled backwards towards its back position and the blade extended in the distal end of the instrument.
Figure 17:
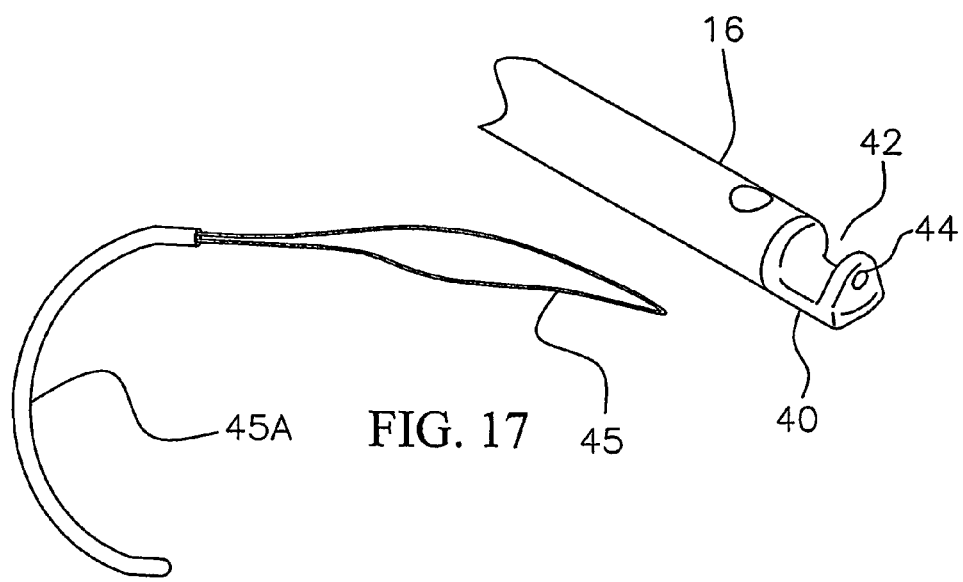
FIGS. 17-20 are partial perspective views of the distal end of the instrument of FIG. 1 showing the suture hole receiving one suture end with the aid of a wire snare loop.
Figure 18:
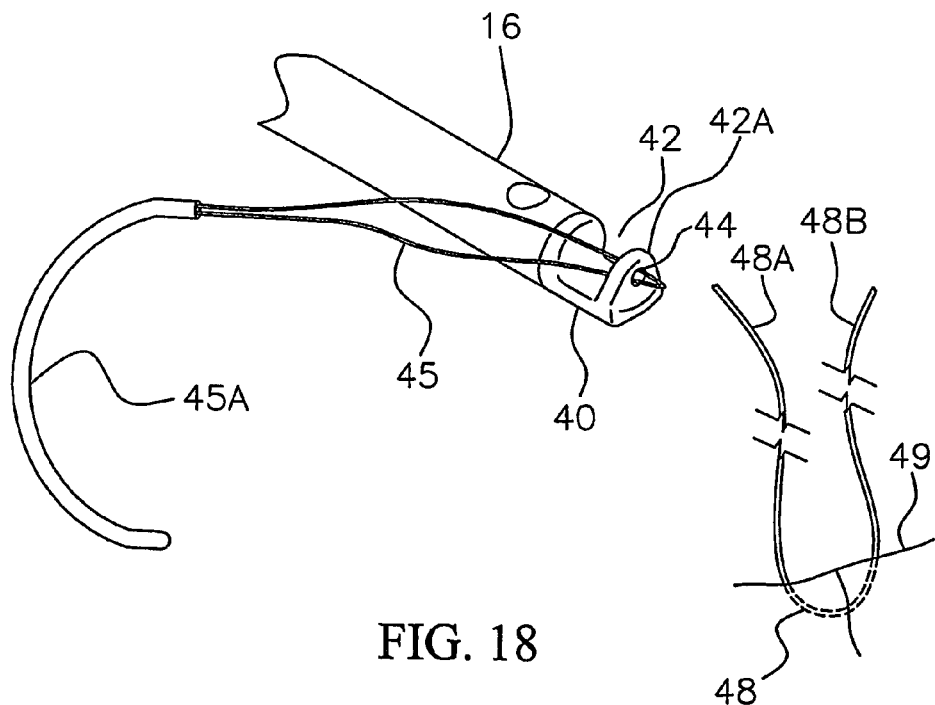

Near open end 18b, a first opening or hole 46 and a second opening or slot 47 (FIG. 6) is provided in tube 18 through which the two ends 48A and 48B of loop of suture 48 may be located after knots 48C are placed in the suture, as shown in FIGS. 3, 3A, and 3B. Opening 47 is shown in dashed in FIGS. 1 and 1A. Opening 46 may be smaller than opening 47, and opening 47 may extend longer along tube 18 than opening 46 to facilitate drawing of suture ends 48A and 48B therethrough along the outside of shaft 12 toward housing 14. As shown in FIGS. 15 and 15A, when retracted in tube 18 by the actuator member 22 being in its forward position, the drive tube 30 coupled to the actuator member 22 locates the blade 38 of blade driver 36 behind openings 46 and 47 in the tube 18. As shown in FIGS. 16 and 16A, by pulling the actuator member 22 towards handle 14A of the housing 14 (as indicated by arrow 19), the drive tube 30 and the blade 38 coupled thereto is advanced forward of the holes 46 and 47 (this movement is indicated by arrows 19A, 19B, and 19C). Both suture ends 48A and 48B when passed through holes 46 and 47 are substantially perpendicular to the length (long axis) of the shaft at the distal end, and in the path of the blade 38. In this manner when suture ends 48A and 48B pass into opening 46 and exit opening 47, cutting or trimming of such ends can be achieved near knot(s) 48c, as shown in FIG. 16A.

Various cross-sectional views of the instrument 10 are provided in FIGS. 7-14.

The shaft 12 of the instrument 10 is preferably size to pass through a channel 52 of a shaft 50A of an endoscope, such as nephroscope 50, as shown in FIG. 3. Nephroscope may be a typical nephroscope having an optical imaging system to view the operation of the instrument 10. However, the instrument may be used with other types of endoscope, or other imaging systems for laparoscopic or other surgical procedures, or without an endoscope.

Figure 19:
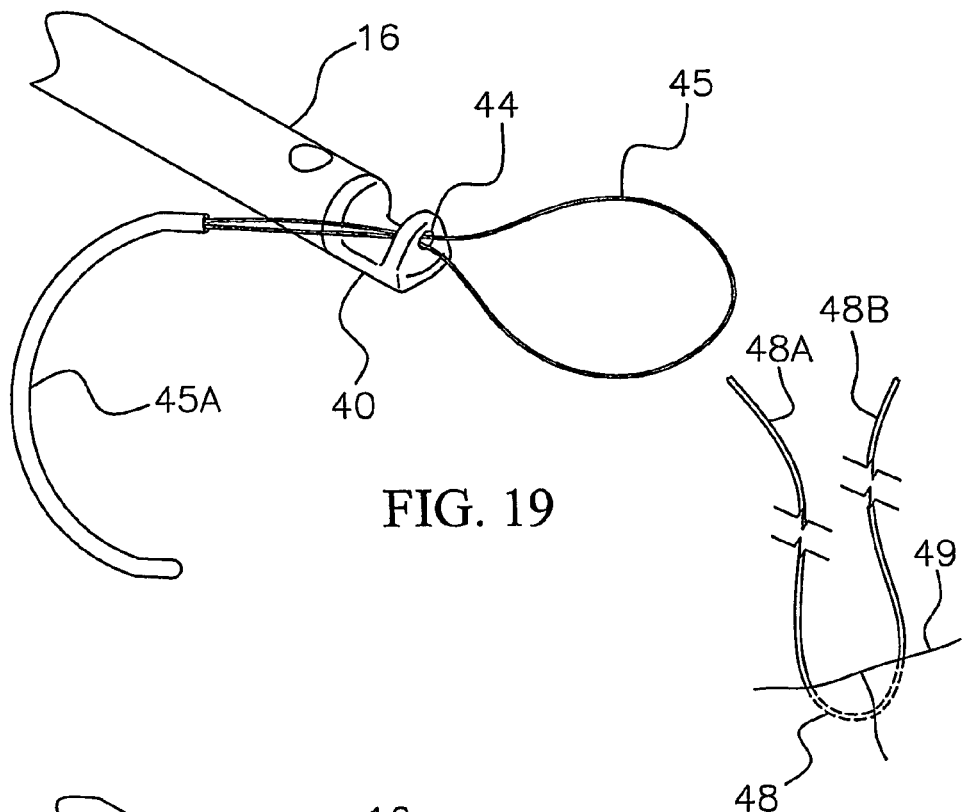
Figure 20:
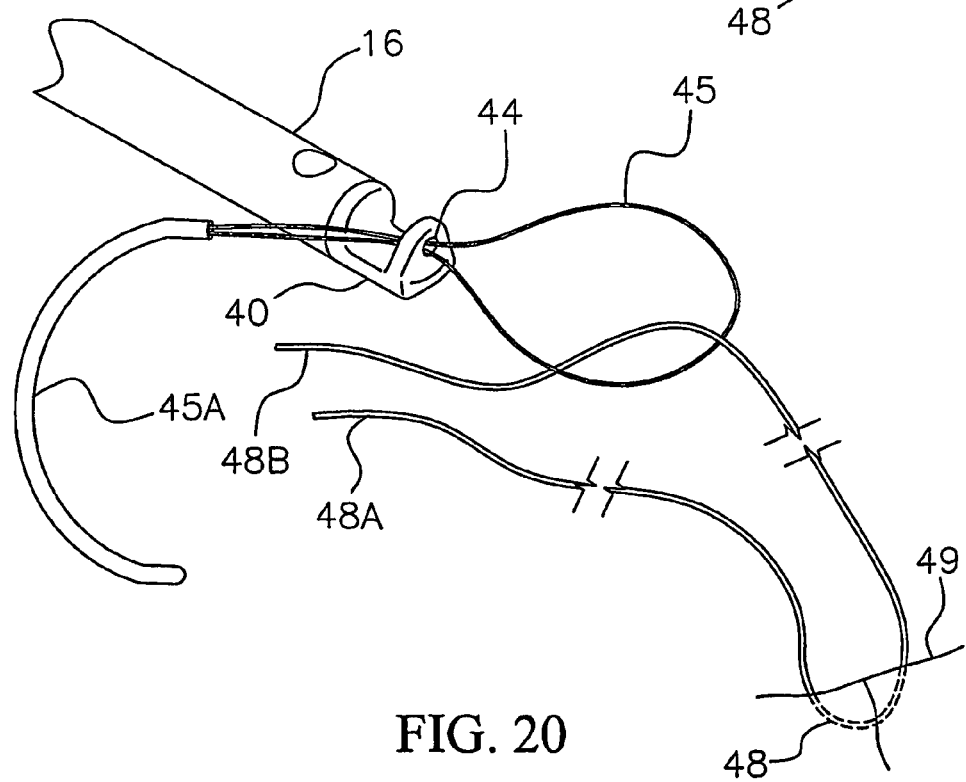
Figure 21:
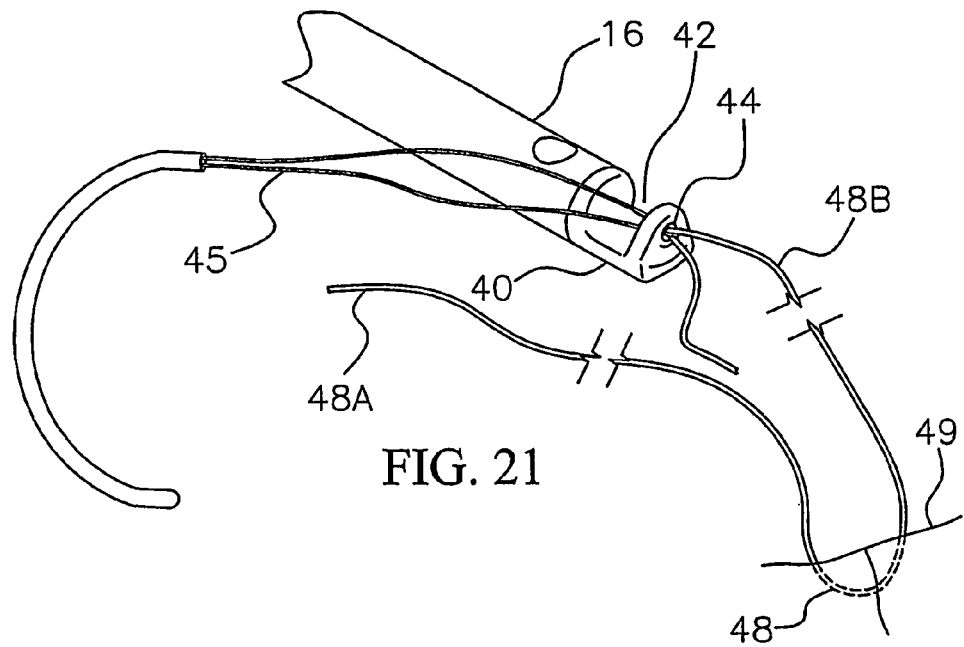
FIGS. 21 and 22 are partial perspective views of the distal end of the instrument of FIG. 1 showing the suture end partially pulled through the suture hole with the aid of the wire snare loop of FIGS. 17-20.
Figure 22:
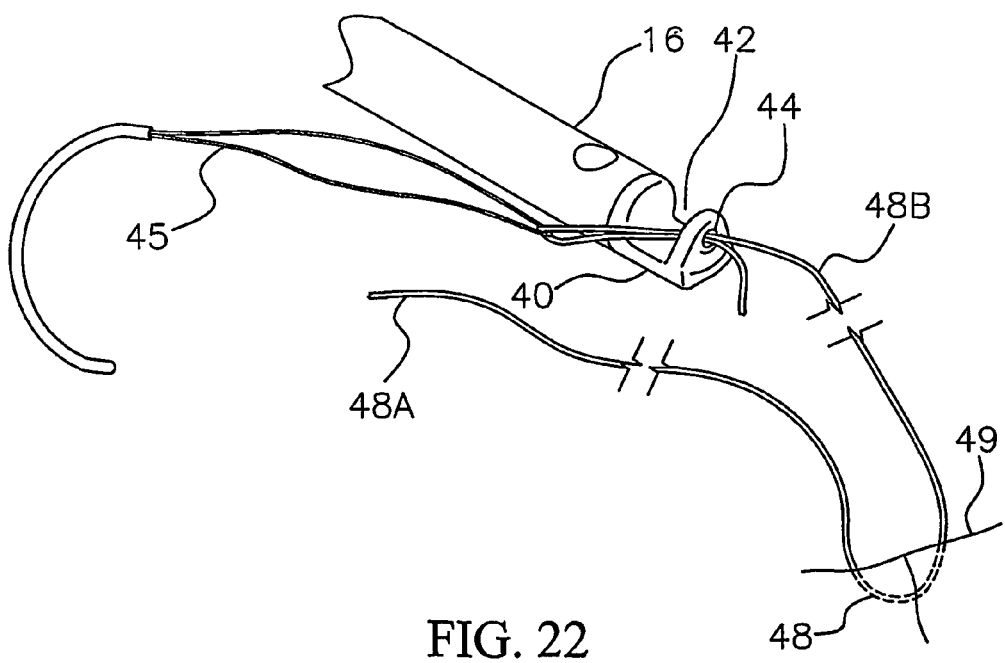
Figure 23:
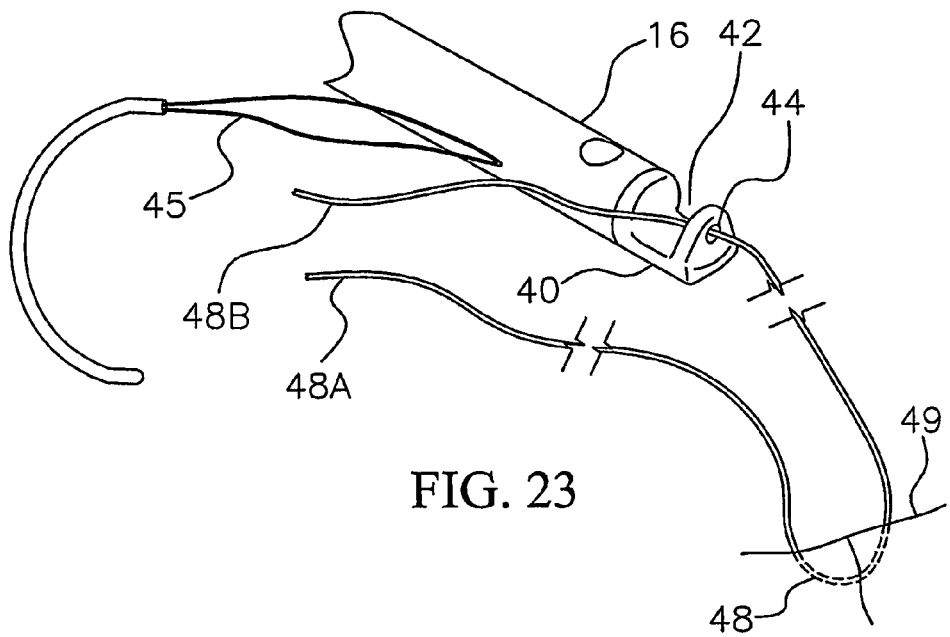
FIG. 23 is a partial perspective view of the distal end of the instrument of FIG. 1 showing one suture end completely through the instrument's suture hole and now free from the wire snare loop of FIGS. 17-22.
Figure 24:
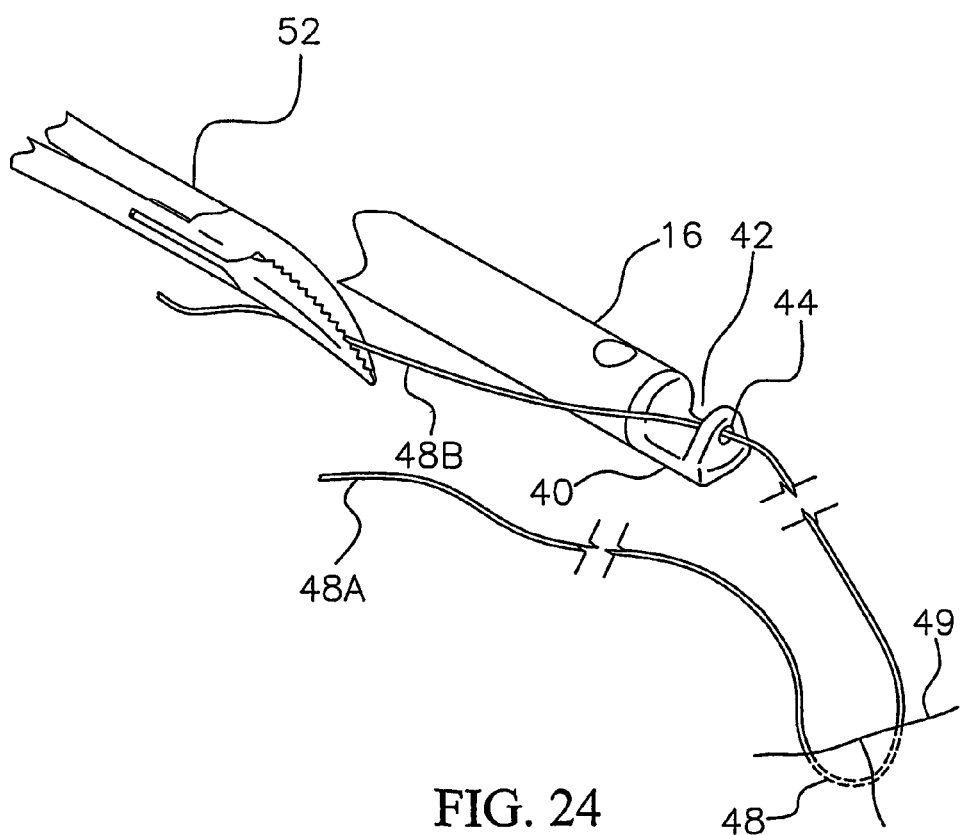
FIG. 24 is a partial perspective view of the distal end of the instrument of FIG. 1 showing one suture end passed through the instrument's suture hole being clamped.
Figure 25:
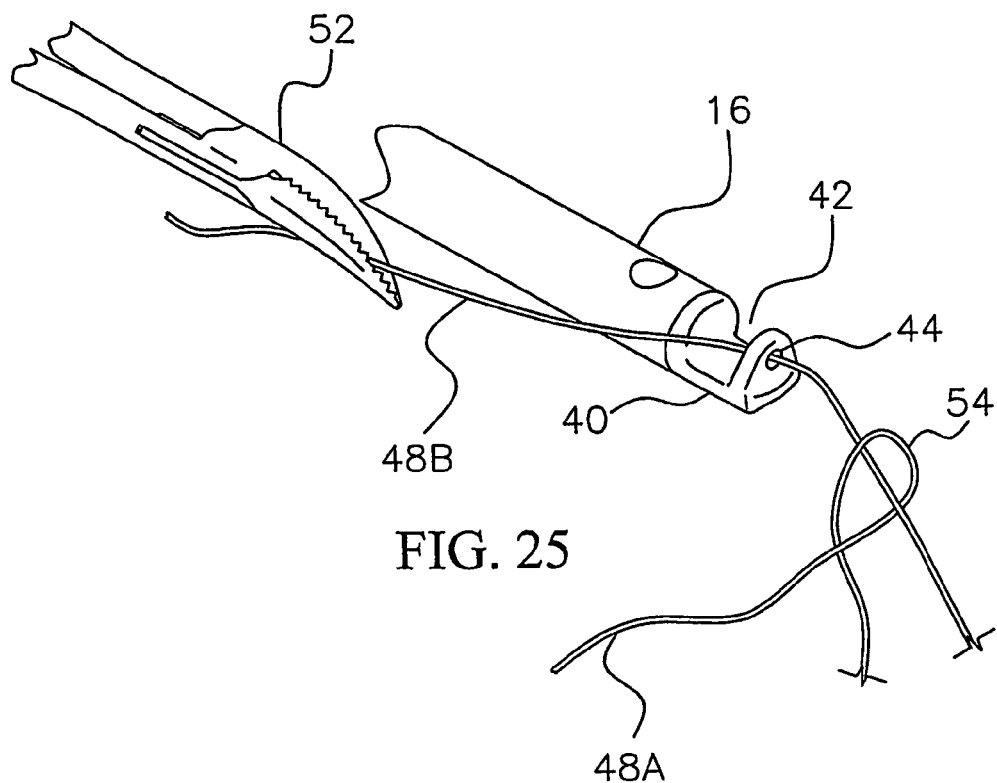
FIGS. 25 and 26 are partial perspective views of the distal end of the instrument of FIG. 1 showing the free end of the suture being wrapped with the first throw of the knot.
Figure 26:
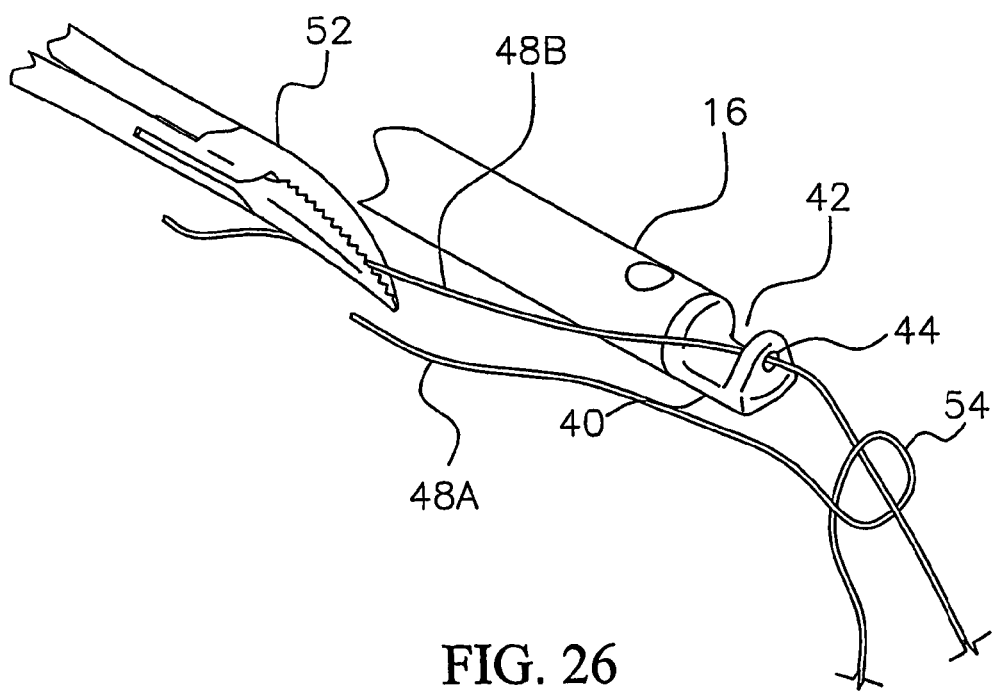
Figure 27:
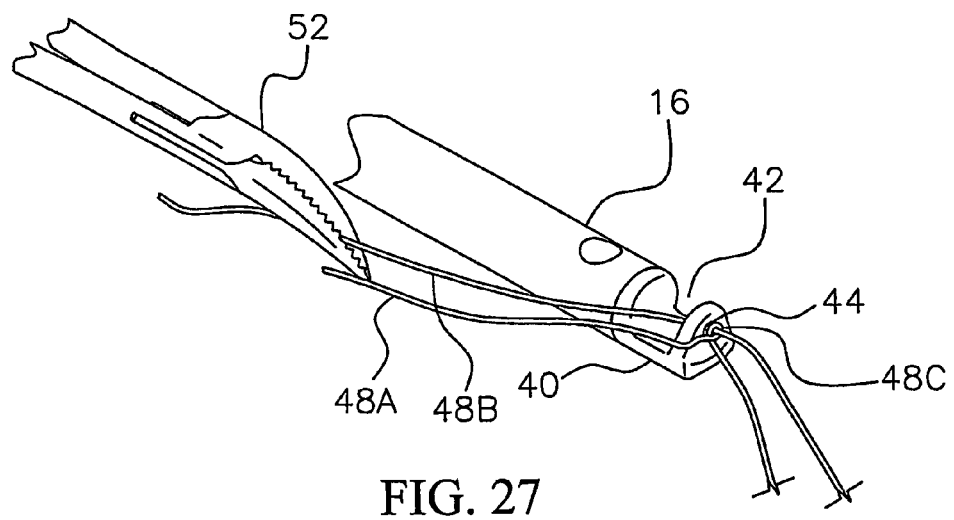
FIG. 27 is a partial perspective view of the distal end of the instrument of FIG. 1 showing the instrument being used to push the knot towards a wound closure site in the tissue.
Figure 28:
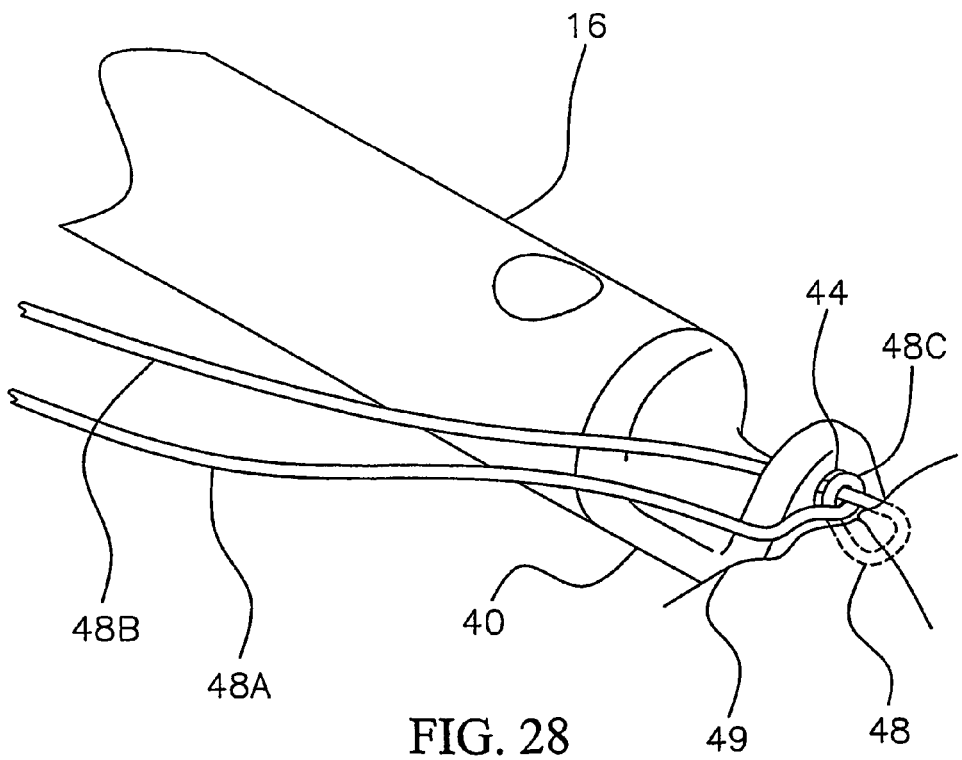
FIG. 28 is a partial perspective view of the distal end of the instrument of FIG. 1 showing the knot as it is being slid down to the wound closure site in the tissue.
Figure 29:
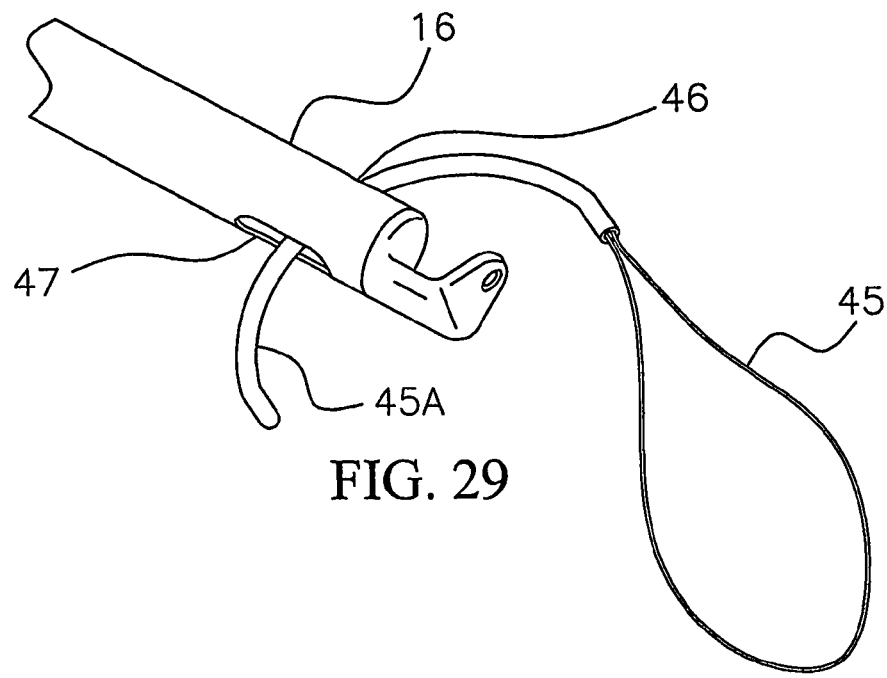
FIG. 29 is a partial perspective view of the distal end of the instrument of FIG. 1 showing the curved handle of the suture snare being introduced through the two openings at the distal end.
Figure 30:
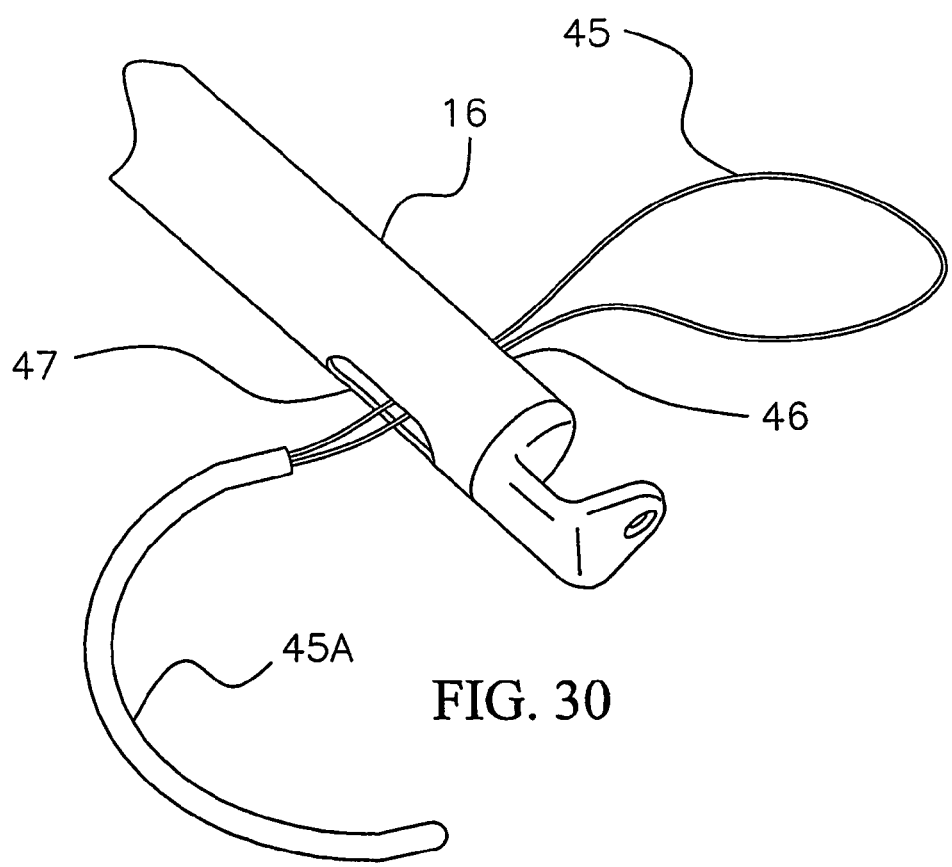
FIG. 30 is a partial perspective view of the distal end of the instrument of FIG. 1 showing the suture snare of FIG. 29 in place ready to receive suture.
Figure 31:
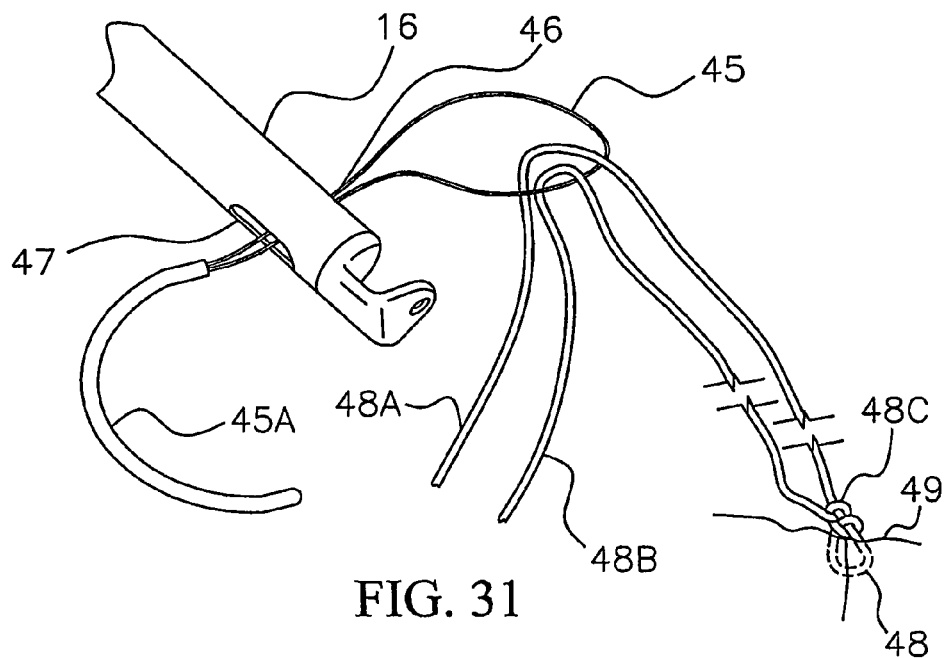
FIG. 31 is a partial perspective view of the distal end of the instrument of FIG. 1 showing the two end of the suture being loading into the suture snare of FIGS. 29 and 30.
Figure 32:
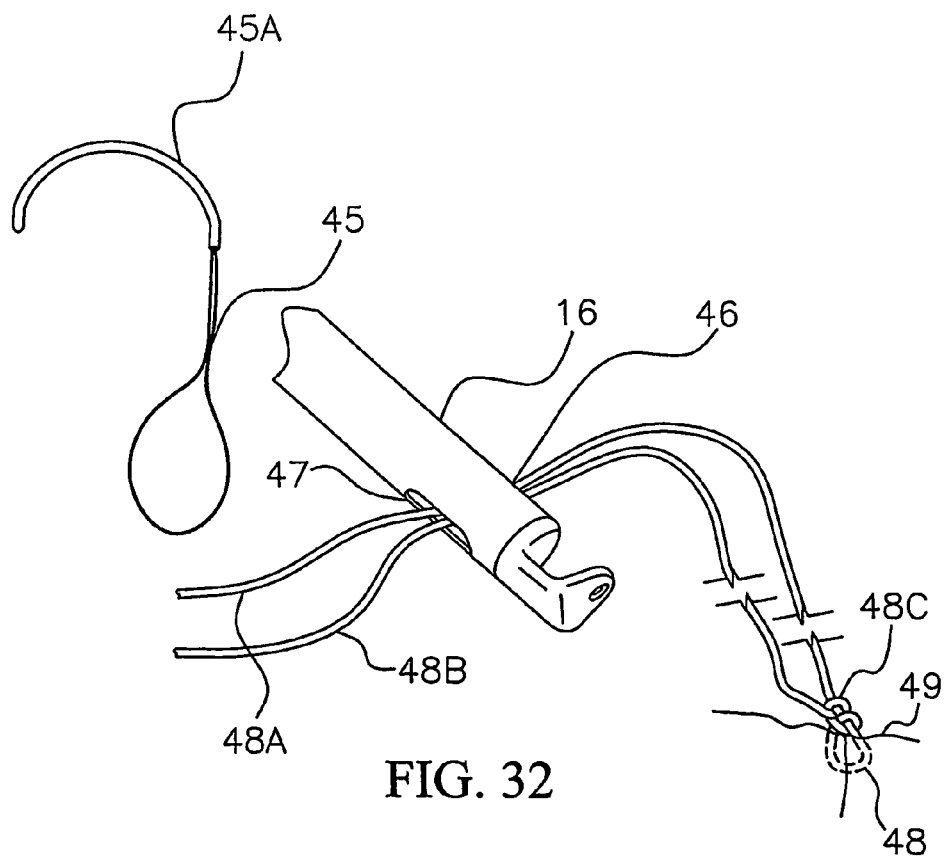
FIG. 32 is a partial perspective view of the distal end of the instrument of FIG. 1 showing the suture now through the trimming holes at the end of the instrument and free from the suture snare of FIGS. 29-31.
Figure 33A:
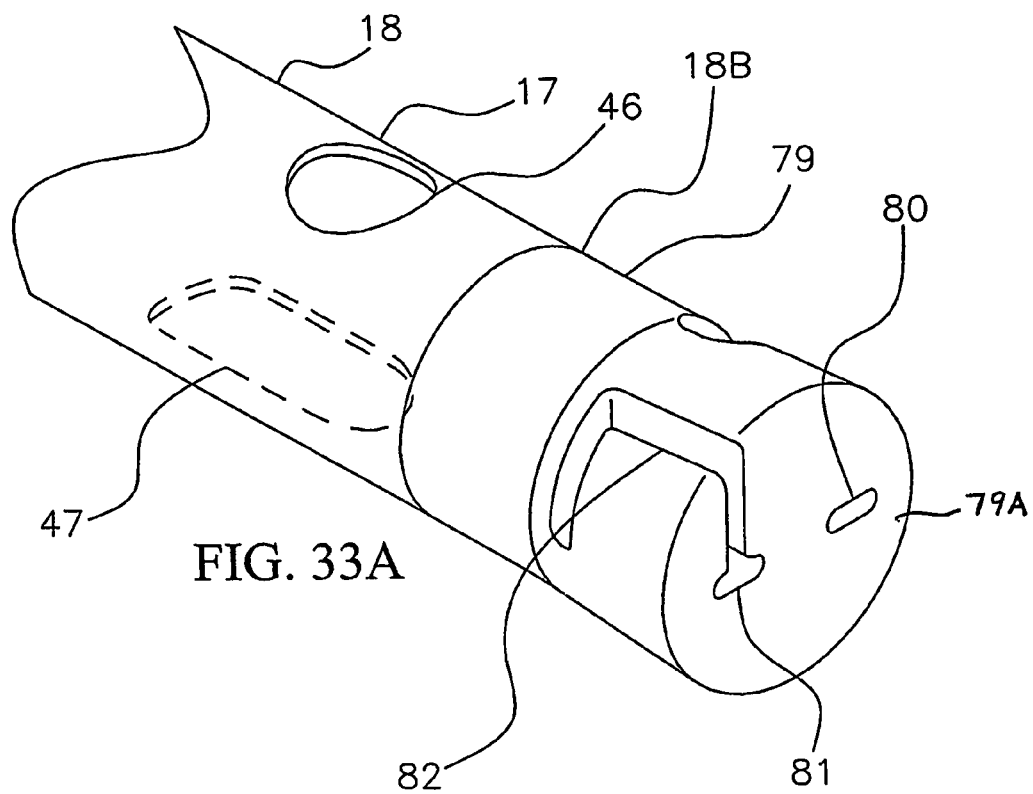
FIG. 33A is a partial perspective view of the right side of the distal end of another embodiment of the instrument of the present invention which is the same as FIG. 1 except for the distal tip member of the instrument.
Figure 33B:
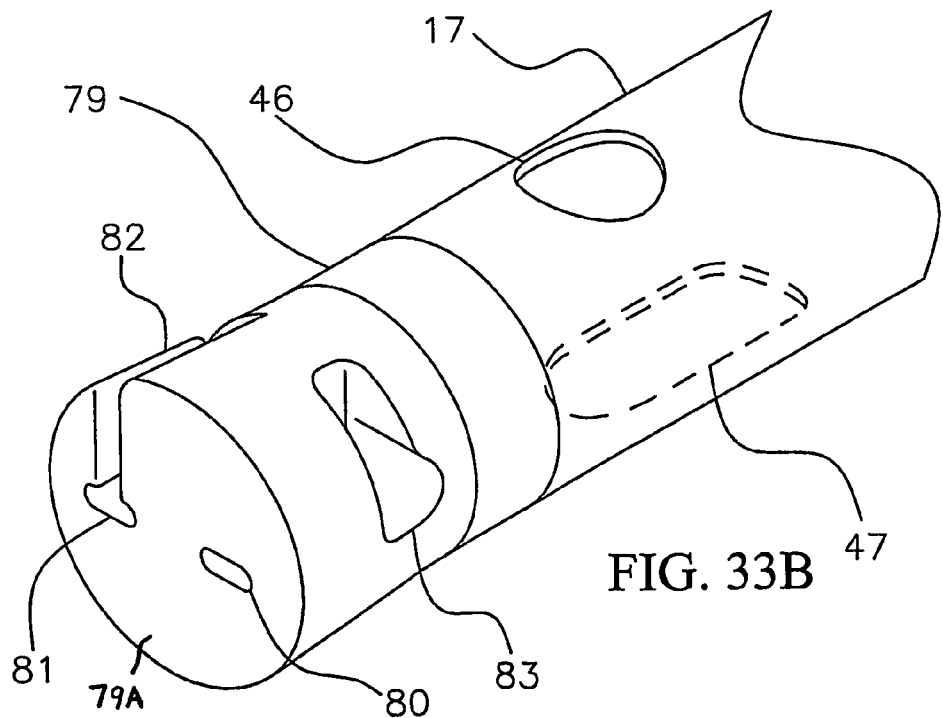
FIG. 33B is a partial perspective view of the left side of the distal end of the instrument in FIG. 33A.
Figure 34A:
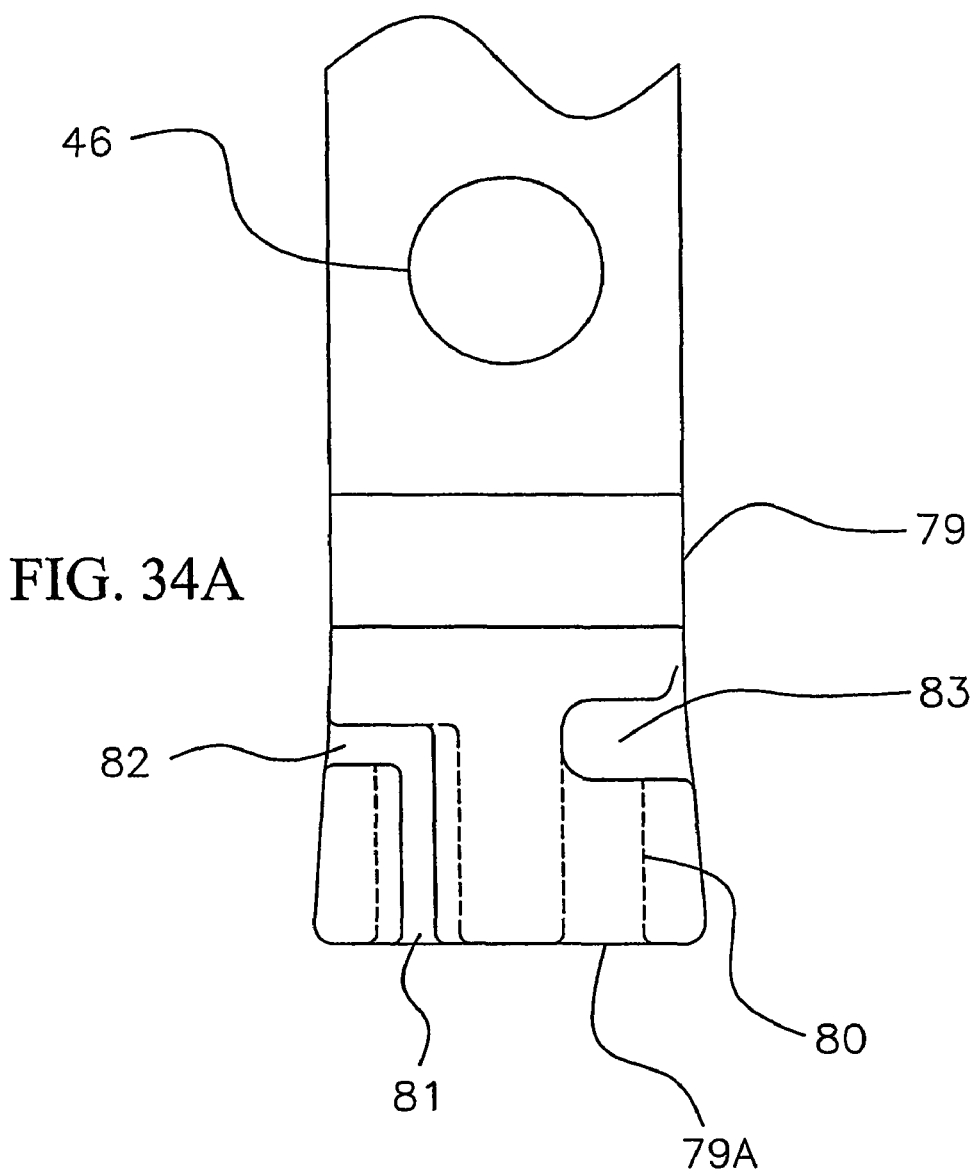
FIG. 34A is a top view of the distal end of the instrument of FIG. 33A.
Figure 34B:
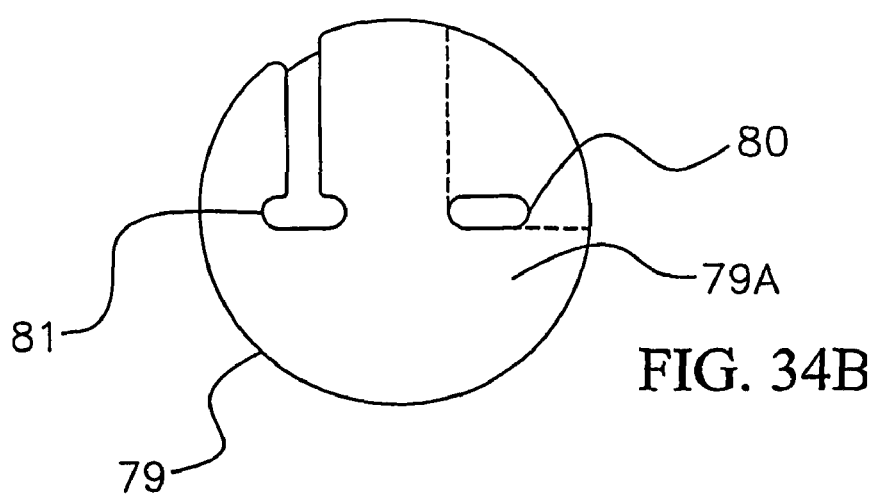
FIG. 34B is an end view of the distal tip member of the instrument of FIG. 33A.

Referring to FIGS. 16, 16A, and 17-32 and, the operation of the instrument 10 is shown for assisting in forming knots in a loop of suture having two free ends extending from tissue and then trimming the free ends from such knots. As described earlier, a guide loop 45 is first passes through hole 44 of the distal tip 40 (FIGS. 17 and 18), and one of the free ends 48B of the suture 48 is passed through the guide loop 45 (FIGS. 19 and 20). The guide loop 45 is then pulled through the hole 44 drawing the free end 48B of suture 48 through hole 44 (FIGS. 21 and 22) and the guide loop is removed (FIG. 23). A clamp 52 is then applied to the free end of suture 48B (FIG. 24). The other end 48A of the suture is looped (e.g., loops 54) around the end 48B of suture between hole 44A and the tissue 49 to form a knot 48C (FIGS. 25-27). The instrument 10 is then advanced forward, while applying tension on end 48b, i.e., pulling back slightly on the clamped end 48B of the suture, thereby pushing the knot 48C adjacent the tissue 49 (FIG. 28). To place another knot, the instrument is pulled back slightly such that the end 48A of the suture may again be looped around the end 48B to form another knot 48C, and the instrument is similarly advanced to push the knot onto the tissue 49. When no more additional knots are needed, the clamp 52 is removed, and the instrument is removed drawing the end 48B of suture out of hole 44. The guide loop 45 is then passed through openings 47 and 46, the two free ends 48A and 48B extending from knot(s) 48C are then passed through the guide loop 45, and the guide loop 45 is then retracted through openings 46 and 47 drawing the two ends 48A and 48B of suture through these openings (FIGS. 29-32). A surgeon holds the free ends 48A and 48B guides the instrument's distal end 18 adjacent to the site of the closed suture, i.e., adjacent the knot(s) 48C made earlier, and while applying slight tension on the free ends 48A and 48b, the actuator member 22 is pulled back advancing the blade 38 and trimming the free ends 48A and 48B of suture, as shown in FIGS. 16 and 16A. The instrument 10 may then be removed from the body of the patient.

The instrument 10 provides the combination of an optimized remote knot pusher and suture trimming device. The contoured narrow hole 44 for sliding a suture loop of a knot down to a wound closure site, precluding the suture loop from slipping into the narrow hole and jamming. The wire snare 45 facilitates loading of the suture through the distal hole 44, conveniently and easily under realistic operating room conditions. The instrument 10 also provides a cutaway window or cavity 42 at the distal tip member 40 to enhance knot placement and tying visualization so that the suture can be seen both from the side and above throughout the knot tying process, such as by an imaging means, such as an endoscope, nephroscope, or the like for viewing distal end 16. To enable suture cutting, this instrument 10 has openings 46 and 47 at distal end 16 through which both tails (ends 48A and 48B) of the suture can be passed once the knot tying is complete. With the suture pulled through these openings and under appropriate tension, the actuator member 22 is squeezed to neatly trim off excess suture tails. The instrument 10 also has a pistol grip handle with its orientation fixed relative to the distal end 16, so that the user readily knows where the distal tip member 40 of the instrument and the hole 44 of the instrument are relative to the handle. The shaft 12 of the instrument may be passed into the body of a patient accessible through ports or cannulas, such as used in laproscopic procedures.

Referring to FIGS. 33A-34B, another embodiment of instrument 10 is shown, which is the same as described above, except that the distal end of the instrument has a distal tip member 79 instead of distal tip member 40. Distal tip member 79 has two suture receiving passageway slots or openings 80 and 81, rather than a single suture receiving hole 44. As best shown in FIGS. 33A, 33B, 34A and 34B, slot 80 extends from the distal front surface 79A of the distal tip member 79 to a cavity or opening 83 along the left side of distal tip member 79. Slot 81 extends from surface 79A, and another slot 82 is provided along the top and right side of the distal tip member 79 extending to slot 81, thereby providing an open sided (or non-circumferentially enclosed) slot, whereas slot 80 is non-open sided (or circumferentially enclosed). The distal tip member 79 may be of plastic, or of metal, such as stainless steel, and manufactured using electrical discharge machining (EDM) processes. The distal tip member 79 is received in tube 18, similar to distal tip member 40. The diameter of distal tip member 79 may optionally increase slightly from its coupling to tube 18 distally towards end 79A, as illustrated for example in FIG. 34A. In these figures, the distal end having the distal tip member of this embodiment is labeled 17. One end of suture 48A or 48B can be received through open-sided slot 81, via slot 82, while the other end of the suture can be received through the non-open sided slot 80. For purposes of illustration the distal tip member edges are shown relatively straight, however they are preferable smoothed or rounded to avoid damaging tissue or suture.

Figure 38B:
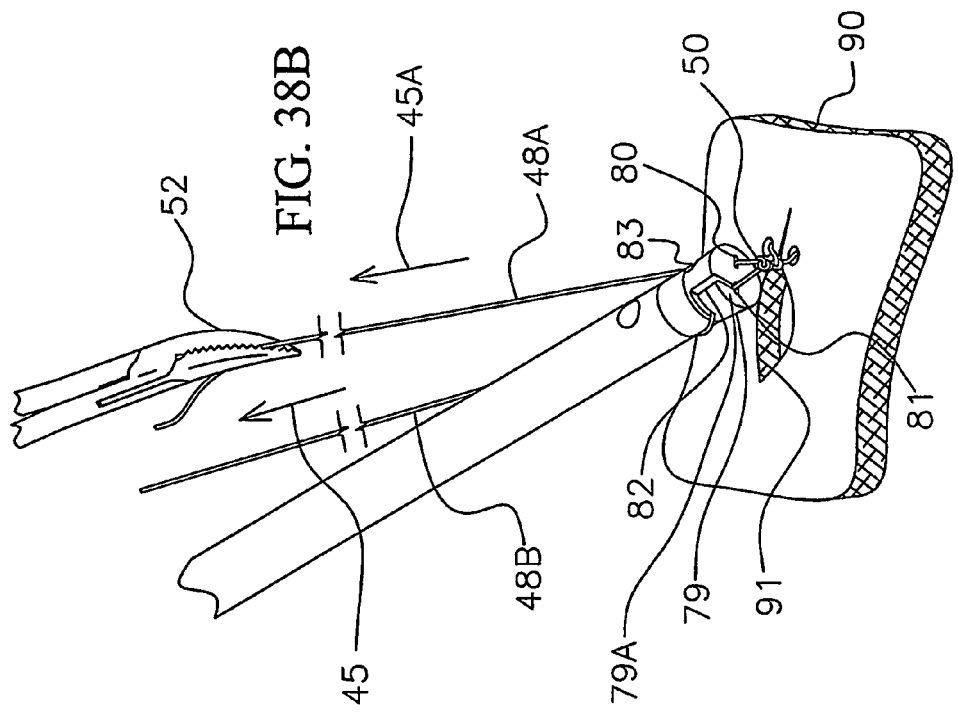
FIG. 38B is a right perspective view of the distal tip member of the instrument of FIG. 33A showing the knot now at the wound closure site and both suture ends simultaneously pulled to secure the knot.
Figure 38A:
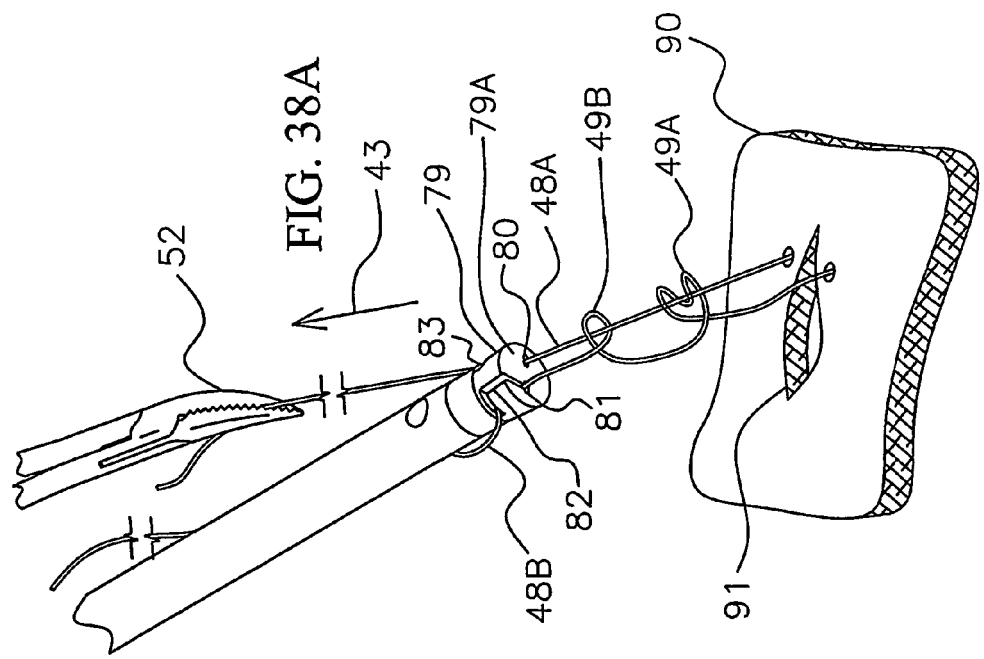
FIG. 38A is a right perspective view of the distal tip member of the instrument of FIG. 33A with a clamp pulling the suture through the non-open sided slot while the distal tip member guides the loops towards the wound closure site.
Figure 39:
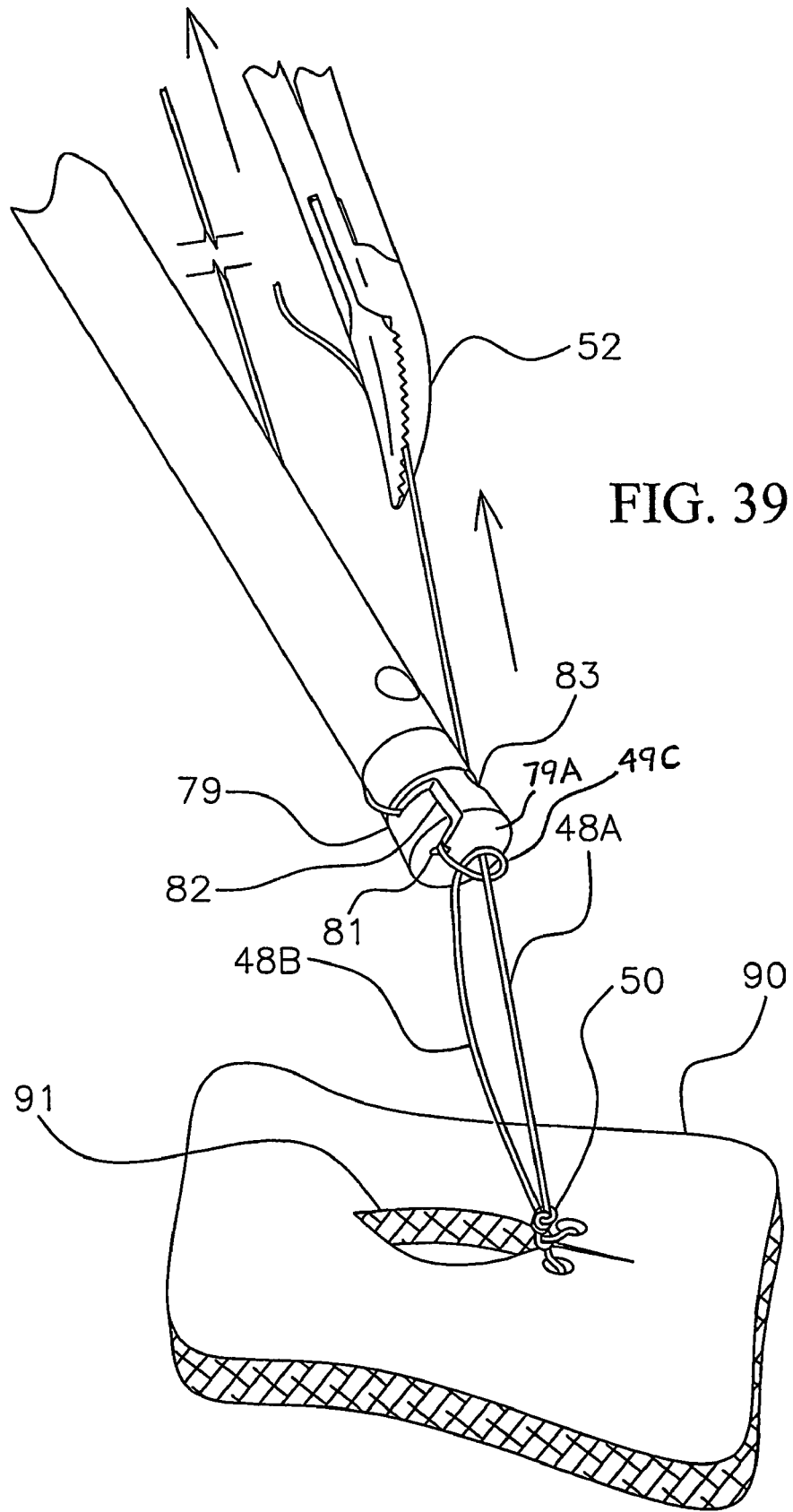
FIG. 39 is a right perspective view of the distal tip member of the instrument of FIG. 33A showing the sliding of additional loops of suture as desired onto the knot to further secure the wound closure site.

Referring to FIGS. 35A-38B, end 48A of suture 48 is shown placed through slot 80 of the distal tip member 79 with the aid of wire snare 45 having a curved handle 45A. First, wire snare 45 is passed through cavity 83 into slot 80 and then exits slot 80 at surface 79A of the distal tip member 79 (FIG. 35A). Next, by pulling on handle 45A wire loop 45 and its ensnared suture end 48A is drawn back through non-open sided slot 80 and cavity 83 (FIG. 35B). Once drawn through slot 80 and cavity 83, the suture end 48A is released from the wire snare (FIG. 35C) and a clamp 52 is placed on that end (FIG. 36A). In FIG. 36A, at a location between the wound site and the distal tip member 79, suture end 48b is passed twice around suture end 48A to create a double loop 49A. In FIG. 36B, an additional single loop 49B of suture end 48B is placed around suture 48A between the double loop 49A and the distal tip member 79. Once the loops are formed, the suture end 48B is received in slot 81 via insertion through slot 82 (FIG. 37A). The suture end 48B is now securely in slot 81 and then at least partially wrapped around the distal end 17 of shaft 12, as shown in FIG. 37B. By pulling on clamp 42 (in direction indicated by arrow 43), but without tensioning suture end 48B, suture end 48A is drawn away from the wound 91 in the tissue and loops 49A and 49B are pushed by distal tip member 79 to slid along suture end 48A towards the wound 91 to form a knot at the wound closure site 91 (FIGS. 38A). The loops are shown loose for purposes of illustration, in actual use the loops are smaller and adjacent to the surface 79A of distal tip member 79 between slots 80 and 81. Once the knot is at the wound closure site 91, and the tissue edges have been appropriately apposed, pulling on suture end 48B (in direction indicated by arrow 45), as well as suture end 48A (in direction indicated by arrow 45A), causes this knot 50 to cinch down and lock a secure enough holding force to enable subsequent know tying without loss of tissue apposition or knot slippage (FIG. 38B). FIG. 39 shows placement of an additional loop 49C on top of initial loops to further secure the knot; more additional loops can be placed as desired. Although this knot is described as being formed with the add of instrument 10 of this embodiment, this method of tying a knot may also be used with a conventional knot pusher instrument having a hole or passageway through which one end of the suture from a wound site is received.

One advantage of this process of constructing a surgical knot is that it permits the user to place the knot on to the wound closure 91 and appropriately appose the wound edge by pulling only on the clamped end of the suture 48A. Once the correct tissue apposition is achieved, the user can pull on the free end of the suture 48B to lock the knot 50 down. Locking down this initial double loop 49A with single loop 49B alone provides a knot with adequate holding force, at least temporarily, to hold together many types of wound closures. For example, this knot made with 2-0 STRONGSORB® suture by LSI SOLUTIONS, INC., achieves an average tissue holding strengths of approximately 0.5 kg knot holding force to temporarily secure and tissue edges together. Subsequent throws (i.e., the single loop 49B) on top of the initial double loop 49A then single loop knot will add additional knot holding force up to the native strength of the suture (e.g., with 2-0 STRONGSORB®, up to 5 to 6 kg tensile pull). It is believed that no other knot can be constructed under such surgical conditions and provides excellent tissue holding force immediately when the first throws (i.e., the double loop 49A, and the single loop 49B) are drawn together by pulling on both ends of the suture.

Once the knots are placed at the wound site, the free ends 48A and 48B of the suture are removed from slots 80 and 81 by pulling the instrument 10 away from the tissue site until the end 48A and 48B exit slots 80 and 81. The ends 48A and 48B may then be drawn through openings 46 and 47, and then cut by the instrument 10 similar to that describe earlier.

From the foregoing description, it will be apparent that an instrument, method, and system is provided for assisting remote placement of tied surgical knots and trimming of the suture away from the knot. Variations and modifications in the herein described instrument, method, and system in accordance with the invention will undoubtedly suggest themselves to those skilled in the art. Accordingly, the foregoing description should be taken as illustrative and not in a limiting sense.

The invention claimed is:

1. An instrument for remote placement of knots in a loop of suture having first and second ends extending through tissue and trimming of suture away from said knots comprising:

a shaft having a distal end;

a distal tip at said distal end having means for facilitating the formation of one or more knots in the suture extending from the tissue, in which said distal tip of said shaft when moved forward pushes said formed one or more knots for placement to the tissue;

two openings at said distal end of said shaft through which is receivable two ends of the suture extending from said placed one or more knots; and means for cutting positionable to cut said suture extending through said openings, wherein said two openings represent first and second openings, said distal tip has a distal surface capable of facing tissue, and said means for facilitating the formation of one or more knots further comprises:

a side cavity in said distal tip;

a third opening extending from said distal surface of said distal tip, and a passageway extending from said third opening to said cavity, in which said first end of said suture is extendable through said third opening and said cavity via said passageway, wherein said passageway represents a first passageway, and said distal tip further comprises:

a fourth opening extending from said distal surface of said distal tip;

a fifth opening along one side of said distal tip;

a second passageway extending from said fourth opening to said fifth opening; and a slot in said distal tip leading to said second passageway into which is receivable the second end of said suture for passage through said second passageway between said fourth and fifth openings.

2. The instrument according to claim 1 wherein said second end of said suture is received through said slot into said second passageway between said fourth and fifth openings after said knots are formed, said second end of said suture is at least partially wrapped around the distal end of the shaft and clamped under tension while the first end of the suture is drawn through the first passageway as the distal end is pushed forward to place said formed knots to the tissue.

3. The instrument according to claim 1 wherein said first passageway represents a non-open sided slot, and said second passageway represents an open-sided slot.

4. A method for remote placement of knots and trimming of suture away from said knots from a loop of suture having first and second ends extending through tissue using a single instrument, said method comprising the steps of:

passing a distal end of the instrument into a body of a patient to locate said distal end near the tissue from which extends first and second ends of said suture;

locating the first end of the suture through a first opening in the distal end of the instrument in which a cavity adjacent said first opening aids in passage of the first end of the suture through said opening;

clamping the first end of the suture passed through said first opening;

forming one or more knots with the second end of said suture about said first end of the suture;

advancing said distal end to said tissue to place said one or more knots adjacent the tissue while the first end of the suture is being drawn through said first opening;

unclamping said first end of the suture;

removing said first end of the suture from said first opening of said distal end;

locating said first and second ends of the suture through second and third openings in said distal end;

moving said distal end adjacent to said one or more knots; and moving a blade at said distal end to cut said first and second ends of the suture located through said second and third openings near said one or more knots.

5. The method according to claim 4 wherein said first opening represents one of a slot or hole.

6. The method according to claim 4 wherein said method further comprises the steps of:

locating said second end of said suture in another opening at said distal end through a passageway open along one side of the distal end prior to said advancing step being carried out;

wrapping the second end of said suture extending from said passageway at least partially around the distal end; and clamping the second end of the suture wrapped around the distal end under tension while said advancing step is carried out.

7. The method according to claim 4 further comprising the step of imaging said distal end of the instrument.

* * * * *